United States Patent [19]

Svendsen et al.

[11] Patent Number: 5,869,438
[45] Date of Patent: Feb. 9, 1999

[54] LIPASE VARIANTS

[75] Inventors: Allan Svendsen, Birkerød; Shamkant Anant Patkar, Lyngby; Erik Gormsen, Virum; Jens Sigurd Okkels; Marianne Thellersen, both of Frederiksberg, all of Denmark

[73] Assignee: Novo Nordisk A/S, Bagsvaerd, Denmark

[21] Appl. No.: 479,275

[22] Filed: Jun. 7, 1995

Related U.S. Application Data

[63] Continuation-in-part of PCT/DK94/00162, Apr. 22, 1994, which is a continuation-in-part of PCT/DK95/00079, Feb. 27, 1995, which is a continuation-in-part of Ser. No. 434,904, May 1, 1995, abandoned, which is a continuation of Ser. No. 977,429, which is a continuation of PCT/DK91/00271, Sep. 13, 1991, abandoned.

[30] Foreign Application Priority Data

Sep. 13, 1990 [DK] Denmark ................................ 2194/90
Sep. 13, 1990 [DK] Denmark ................................ 2195/90
Sep. 13, 1990 [DK] Denmark ................................ 2196/90
Apr. 23, 1993 [DK] Denmark ................................ 0466/93
Feb. 22, 1994 [DK] Denmark ................................ 0217/94

[51] Int. Cl.$^6$ .................................................. C11D 3/386
[52] U.S. Cl. .................. 510/226; 435/198; 435/69.1; 435/252.3; 435/320.1; 435/196; 536/23.2; 536/23.7; 530/350; 510/392; 510/305
[58] Field of Search ..................................... 435/198, 196, 435/187–188, 69.1, 252.3, 320.1, 71.1; 424/94.1; 536/22.2, 23.7; 510/305, 226, 392

[56] References Cited

FOREIGN PATENT DOCUMENTS

| 0 305 216 A1 | 3/1989 | European Pat. Off. . |
| 0 407 225 A1 | 1/1991 | European Pat. Off. . |
| WO 95/09909 | 4/1995 | WIPO . |

*Primary Examiner*—Robert A. Wax
*Assistant Examiner*—Tekchand Saidha
*Attorney, Agent, or Firm*—Steve T. Belson; Elias J. Lambiris

[57] ABSTRACT

The present invention relates to lipase variants which exhibit improved properties, detergent compositions comprising said lipase variants, DNA constructs coding for said lipase variants, and methods of making said lipase variants.

51 Claims, 10 Drawing Sheets

(4 of 10 Drawing Sheet(s) Filed in Color)

5,869,438

LIPASE VARIANTS

CROSS-REFERENCE TO RELATED APPLICATIONS

This application is a continuation-in-part of Ser. No. PCT/DK94/00162 filed Apr. 22, 1994, PCT/DK95/00079 filed Feb. 27, 1995 and of Ser. No. 08/434,904, filed May 1, 1995, now abandoned, which is a continuation of Ser. No. 07/977,429 filed Feb. 22, 1993, now abandoned, which is a continuation of PCT/DK91/00271 filed Sep. 13, 1991, which are incorporated herein by reference.

FIELD OF INVENTION

The present invention relates to lipase variants with improved properties, DNA constructs coding for the expression of said variants, host cells capable of expressing the variants, and methods of producing the variants by cultivating said host cells.

BACKGROUND OF THE INVENTION

For a number of years lipolytic enzymes have been used in detergents to remove lipid or fatty stains from clothes and other textiles.

For instance, various microbial lipases have been suggested as detergent enzymes. Examples of such lipases include a *Humicola lanuginosa* lipase, e.g., described in EP 258,068 and EP 305,216, a *Rhizomucor miehei* lipase, e.g., as described in EP 238,023, a Candida lipase, such as a *C. antarctica* lipase, e.g., the *C. antarctica* lipase A or B described in EP 214,761, a Pseudomonas lipase such as a *P. alcaligenes* and *P. pseudoalcaligenes* lipase, e.g., as described in EP 218,272, a *P. cepacia* lipase, e.g., as described in EP 331,376, a Bacillus lipase, e.g., a *B. subtilis* lipase (Dartois et al., *Biochemica* et *Biophysica Acta* 1131, pp. 253–260 (1993)), a *B. stearothernophilus* lipase (JP 64/744992) and a *B. pumilus* lipase (EP 91 00664).

Furthermore, a number of cloned lipases have been described, including the *Penicillium camembertii* lipase described by Yamaguchi et al., *Gene* 103, pp. 61–67 (1991), the *Geotricum candidumn* lipase (Shimada et al., *J. Biochem.* 106, 383–88 (1989)), and various Rhizopus lipases such as a *R. delemar* lipase (Hass et al., *Gene* 109, pp. 107–13 (1991)), a *R. niveus* lipase (Kugimiya, *Biosci. Biotech. Biochem.* 56, pp. 716–19 (1992)), and a *R. oryzae* lipase.

The primary structure of a number of lipases has been determined and described in the literature (Boel et al., *Lipids* 23, pp. 701–06 (1988), de Caro et al., *Biochim. Biophys. Acta* 671, pp. 129–38 (1981), Winkler et al., *Nature* 343, pp. 771–74 (1990)). Furthermore, the tertiary structure of a more limited number of lipases has been elucidated (Brady et al., *Nature* 343, 767–70 (1990) and Schrag et al., *Nature* 351, pp. 761–64 (1991)). From these investigations it appears that lipases seem to have certain structural features in common, but that, on the other hand, major structural variations also exist among the lipases.

Other types of lipolytic enzymes include cutinases, e.g., a cutinase derived from *Pseudomonas mendocina* (WO 88/09367), or from *Fusarium solani pisi* (WO 90/09446).

In recent years attempts have been made to prepare lipase variants having improved properties for detergent purposes.

PCT/DK93/00225 describes lipase variants with improved properties, in which an amino acid residue occupying a critical position of the lipase has been modified.

EP 407,225 discloses lipase variants with improved resistance towards proteolytic enzymes, which have been prepared by specifically defined amino acid modifications.

EP 260,105 describe hydrolases in which an amino acid residue within 15 Å from the active site has been substituted.

All of the above mentioned lipase variants have been constructed by use of site-directed mutagenesis resulting in a modification of specific amino acid residues which have been chosen either on the basis of their type or on the basis of their location in the secondary or tertiary structure of the parent lipase.

An alternative approach for constructing mutants or variants of a given protein has been based on random mutagenesis. For instance, U.S. Pat. No. 4,898,331 and WO 93/01285 disclose such techniques.

It is an object of the present invention to prepare lipolytic enzymes having improved washing and/or dishwashing properties.

SUMMARY OF THE INVENTION

The present invention relates to variants of a parent lipolytic enzyme which exhibit improved properties, detergent compositions comprising said lipase variants, DNA constructs coding for said lipase variants, and methods of making said lipase variants.

The present invention also relates to a method of preparing variants of lipolytic enzymes having improved washing and/or dishwashing performance as compared to their parent enzymes. The method is based on random or localized random mutagenesis of DNA sequences encoding a lipolytic enzyme. More specifically, this method comprises (a) subjecting a DNA sequence encoding the parent lipolytic enzyme to random mutagenesis;

(b) expressing the mutated DNA sequence obtained in step (a) in a host cell; and (c) screening for host cells expressing a mutated lipolytic enzyme which has a decreased dependence to calcium and/or an improved tolerance towards a detergent or one or more detergent components as compared to the parent lipolytic enzyme.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

The present invention is described in the following with reference to the appended drawings, in which.

DETAILED DISCLOSURE OF THE INVENTION

Figure 1A:
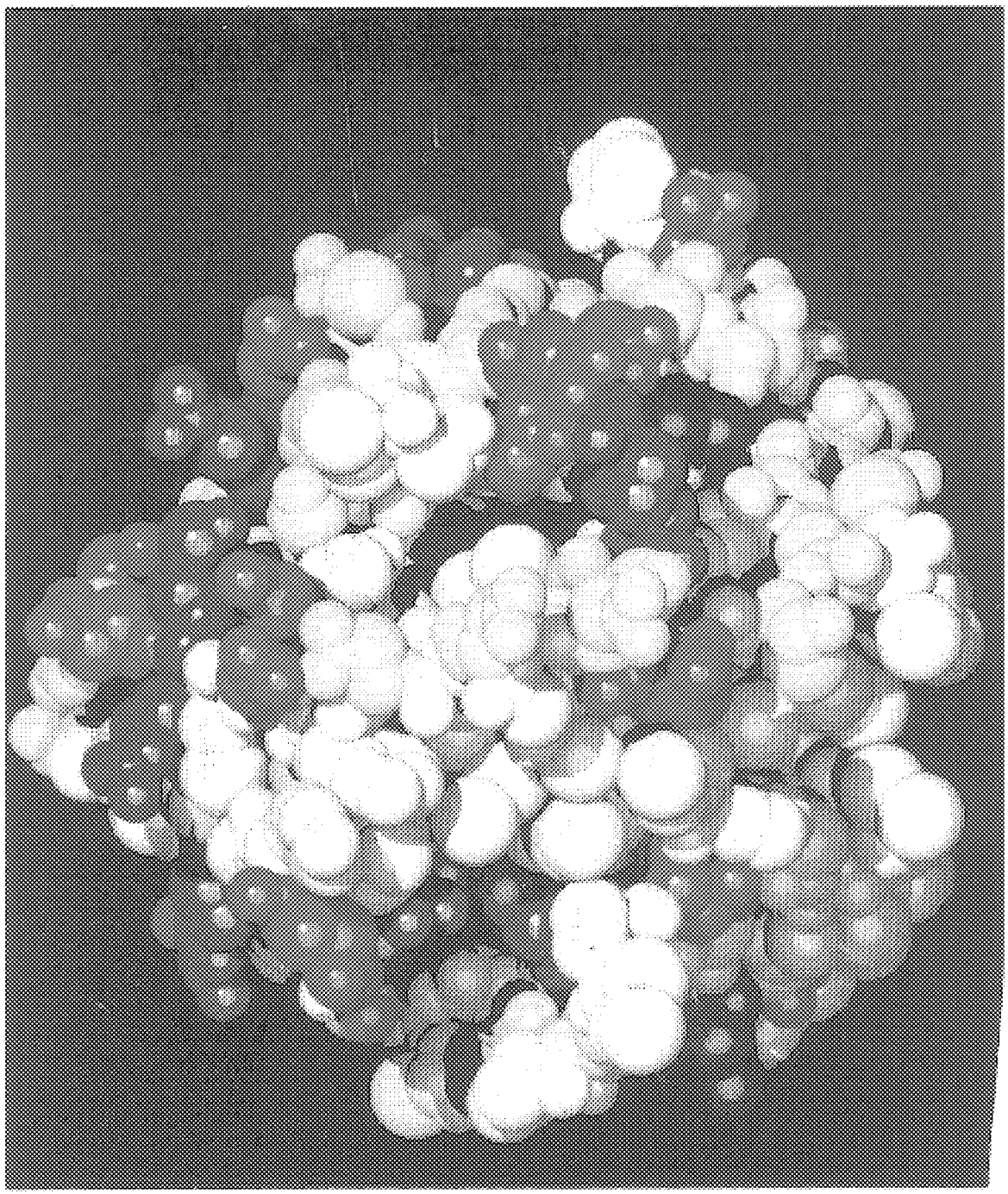
FIGS. 1A and B are computer models showing the three-dimensional structure of the lipid contact zone of the *H. lanuginosa* lipase when the lipase is in inactive (A) and active (B) form, respectively. "White" residues represent hydrophobic amino acids (Ala, Val, Leu, Ile, Pro, Phe, Trp, Gly and Met), "yellow" residues represent hydrophilic amino acids (Thr, Ser, Gln, Asn, Tyr and Cys), "blue" residues represent positively charged amino acids (Lys, Arg and His), and "red" residues represent negatively charged amino acids (Glu and Asp)
Figure 1B:
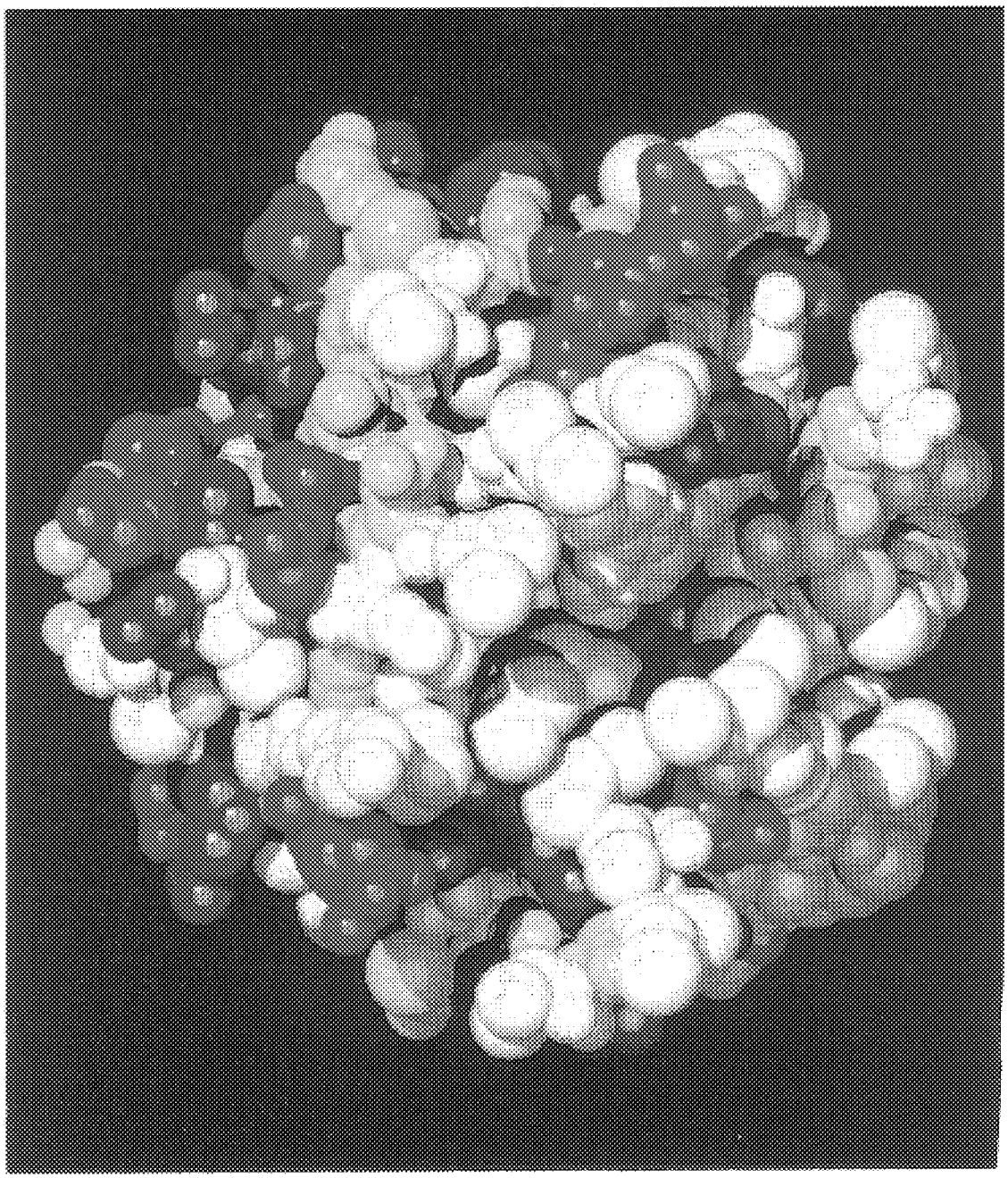
Figure 2A:
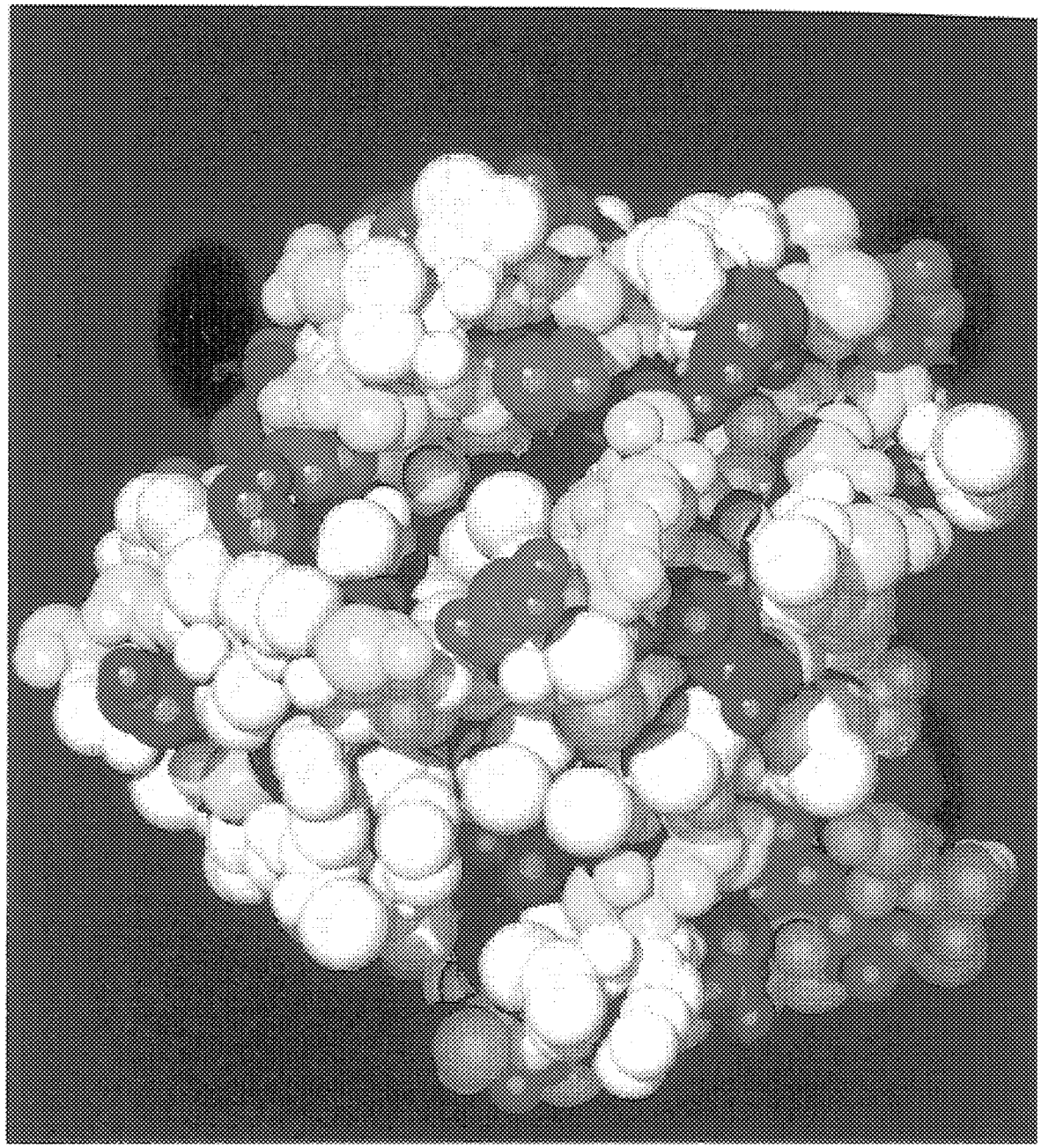
FIGS. 2A and 2B are computer models showing the three-dimensional structure of the lipid contact zone of the *Rh. miehei* lipase when the lipase is in inactive (A) and active (B) form, respectively.
Figure 2B:
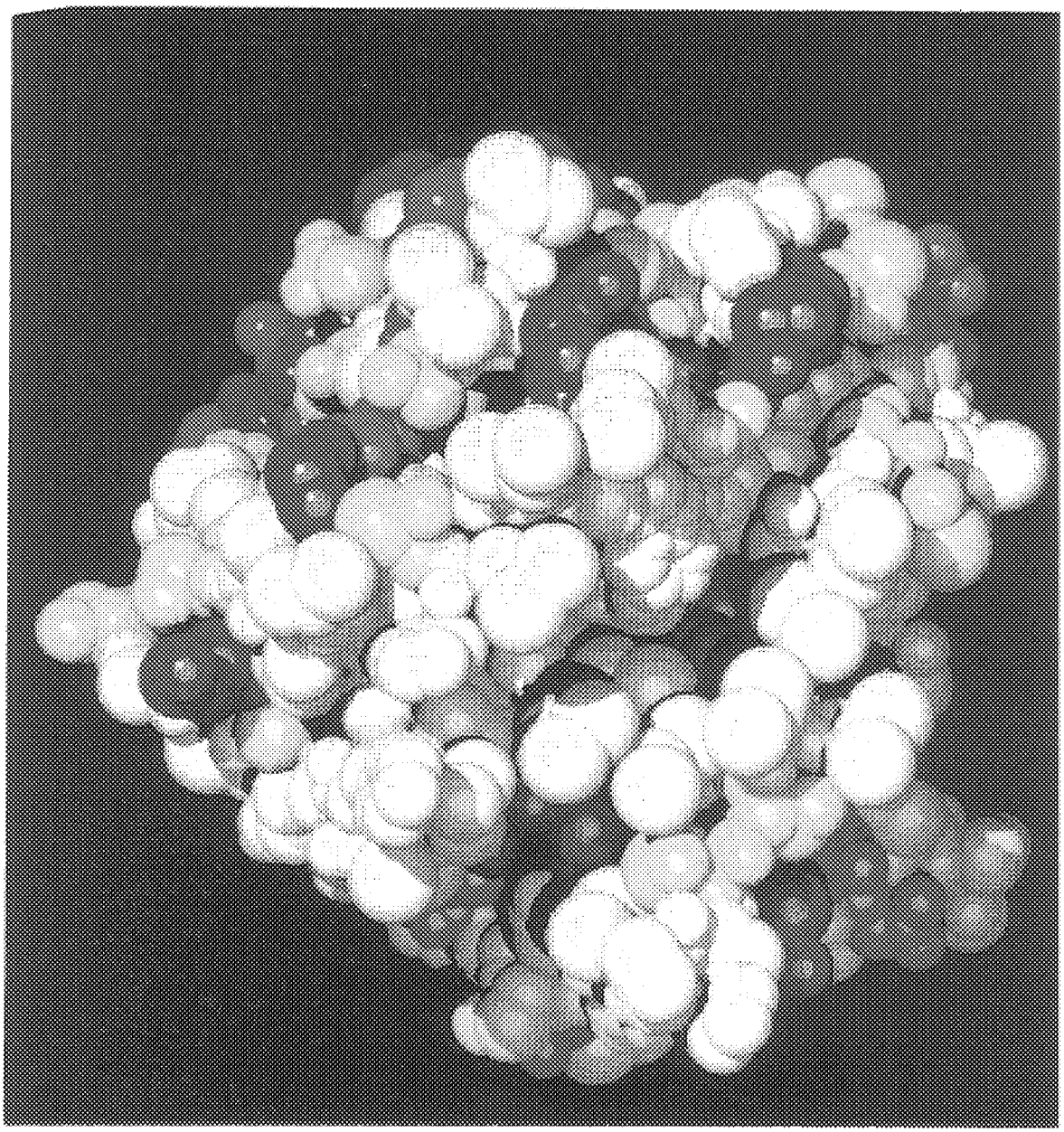

Cloning a DNA sequence encoding a lipase

The DNA sequence encoding a lipase may be isolated from any cell or microorganism producing the parent enzyme in question by use of methods known in the art.

For instance, the DNA sequence may be isolated by establishing a cDNA or genomic library from an organism expected to harbour the sequence, and screening for positive clones by conventional procedures. Examples of such procedures are hybridization to oligonucleotide probes prepared on the basis of the amino acid or DNA sequence of the parent enzyme (if sequence information is available) or of a related lipolytic enzyme (if sequence information as to the parent enzyme is not available) in accordance with standard techniques (cf., Sambrook et al., Molecular Cloning: A Laboratory Manual, 2nd Ed., Cold Spring Harbor, (1989)), and/or selection for clones expressing lipolytic, such as lipase activity, and/or selection for clones producing a protein which is reactive with an antibody raised against a parent lipolytic enzyme.

A preferred method of isolating a DNA sequence encoding a parent lipolytic enzyme to be modified in accordance with the invention from a cDNA or genomic library is by use of polymerase chain reaction (PCR) using degenerate oligonucleotide probes prepared on the basis of the DNA or amino acid sequence of the parent enzyme. For instance, PCR may be carried out using the techniques described in U.S. Pat. No. 4,683,202 or by Saiki et al., *Science* 239, pp. 487–91 (1988).

Alternatively, the DNA sequence encoding the parent enzyme may be prepared synthetically by established standard methods, e.g., the phosphoamidite method described by Beaucage et al., *Tetrahedron Letters* 22, pp. 1859–69 (1981), or the method described by Matthes et al., *The EMBO J*. 3, pp. 801–05 (1984). According to the phosphoamidite method, oligonucleotides are synthesized, e.g., in an automatic DNA synthesizer, purified, annealed, ligated and cloned in appropriate vectors.

Finally, the DNA sequence encoding the parent enzyme may be prepared from DNA of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence encoding the parent enzyme, in accordance with standard techniques.

Site-directed mutagenesis of the lipase-encoding sequence

Once a lipase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the lipase-encoding sequence, is created in a vector carrying the lipase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., *Biotechnology* 2, pp. 646–49 (1984). U.S. Pat. No. 4,760,025 discloses the introduction of oligonucleotides encoding multiple mutations by performing minor alterations of the cassette, however, an even greater variety of mutations can be introduced at any one time by the Morinaga method, because a multitude of oligonucleotides, of various lengths, can be introduced.

Figure 3:
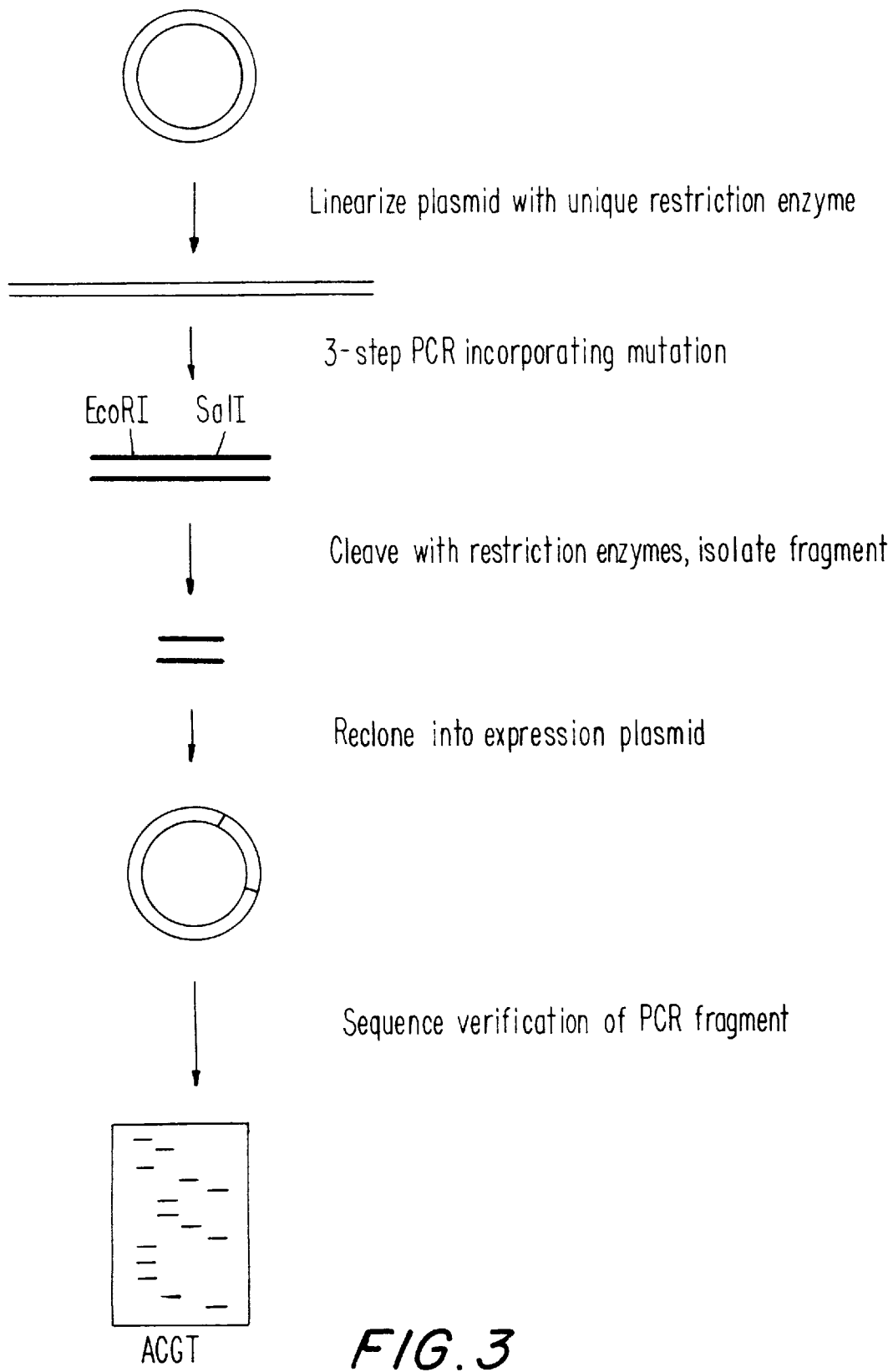
FIG. 3 is a schematic representation of the preparation of plasmids encoding lipase variants by polymerase chain reaction (PCR)

Another method of introducing mutations into lipase-encoding sequences is described in Nelson et al., *Analytical Biochemistry* 180, pp. 147–51 (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid (see also FIGS. 3 and 4 where this method is further outlined).

Random mutagenesis

The random mutagenesis of the DNA sequence encoding the parent lipolytic enzyme to be performed in accordance with step a) of the method of the invention may conveniently be performed by any method known in the art. The random mutations are typically introduced by exposing a large number of copies of the DNA sequence to be modified to a mutagen and then screening for the presence of variants.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose includes ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions wanted to be changed. The doping or spiking may be done so that codons for unwanted amino acids are avoided. The doped or spiked oligonucleotide can be incorporated into the DNA encoding the lipolytic enzyme by any published technique using, e.g., PCR, LCR or any DNA polymerase and ligase.

When PCR generated mutagenesis is used either a chemically treated or non-treated gene encoding a parent lipolytic enzyme is subjected to PCR under conditions that increases the misincorporation of nucleotides (Deshler, *GATA* 9(4), pp. 103–06 (1992), Leung et al., *Technique* 1(1), pp. 11–15 (1989)).

A mutator strain of *E. coli* (Fowler et al., *Molec. Gen. Genet*. 133, pp. 179–91 (1974)), *S. cereviciae* or any other microbial organism may be used for the random mutagenesis of the DNA encoding the lipolytic enzyme by, e.g., transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent lipolytic enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step (b) or the screening step (c). Such amplification may be performed in accordance with methods known in the art, the presently preferred method being PCR generated amplification using oligonucleotide primers prepared on the basis of the DNA or amino acid sequence of the parent enzyme.

Localized random mutagenesis

In accordance with the invention the random mutagenesis may advantageously be located to a part of the parent lipolytic enzyme in question. This may, e.g., be advantageous when a certain region of the enzyme has been identified to be of particular importance for a given property of the enzyme, and which, when modified, is expected to result in a variant having improved properties. Such region may normally be identified when the tertiary structure of the parent enzyme has been elucidated and related to the function of the enzyme.

The localized random mutagenesis is conveniently performed by use of PCR generated mutagenesis techniques as described above or any other suitable technique known in the art.

Alternatively, the DNA sequence encoding the part of the DNA sequence to be modified may be isolated, e.g., by being inserted into a suitable vector, and said part may subsequently be subjected to mutagenesis by use of any of the mutagenesis methods discussed above.

Screening for Host Cells Expressing Desirable Mutated Lipolytic Enzymes

The term "decreased dependence to calcium" is intended to mean that the mutated lipolytic enzyme requires lower amounts of calcium for exhibiting the same degree of activity as the parent enzyme when tested under similar conditions. Preferably, the mutated lipolytic enzyme of the invention is substantially independent of the presence of calcium for exhibiting enzymatic activity. The term "improved tolerance towards a detergent or detergent component" is intended to mean that the mutated lipolytic enzyme is active at higher concentrations of the detergent or detergent component than the parent lipolytic enzyme. Without being limited to any theory the screening for a decreased dependency to calcium is believed to result in variants having an over-all improved performance in that the requirement for calcium may be considered a limiting factor for optimal activity, in particular under conditions where only low amounts of free calcium ions are present. In connection with detergent lipases the free calcium ions required are normally provided from the washing water and thus, the lipolytic activity is dependent on the calcium content of the water.

It will be understood that the screening criteria mentioned in step (c) above have been carefully selected. Thus, without being limited to any theory the screening for a decreased dependency to calcium is believed to result in variants having an over-all improved performance in that the requirement for calcium may be considered a limiting factor for optimal activity, in particular under conditions where only low amounts of free calcium ions are present. In connection with detergent lipases the free calcium ions required are normally provided from the washing water and thus, the lipolytic activity is dependent on the calcium content of the water.

The detergent or detergent component towards which the variant has improved tolerance may be of any type, e.g., as further described below. Preferably, the detergent component is a non-ionic, anionic, kationic, zwitterionic or amphoteric surfactant. Examples of non-ionic surfactants include an alcohol ethoxylate, examples of anionic surfactants include LAS, alkyl sulphate, alcohol ethoxy sulphate and the like.

In particular, it is contemplated that an improved tolerance towards a non-ionic surfactant alcohol ethoxylate, a commercially available example of which is Dobanol®, may be indicative of improved wash performance.

The screening of step (c) is conveniently performed by use of a filter assay based on the following principle:

A microorganism capable of expressing the mutated lipolytic enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g., nylon or nitrocellulose. The topfilter carrying the colonies of the expression organism may be any filter that has no or low affinity for binding proteins e.g., cellulose acetate or Durapore™. The filter may be pretreated with any of the conditions to be used for screening or may be treated during the detection of enzymatic activity.

The enzymatic activity may be detected by a dye, flourescence, precipitation, pH indicator, IR-absorbance or any other known technique for detection of enzymatic activity.

The detecting compound may be immobilized by any immobilizing agent e.g., agarose, agar, gelatine, polyacrylamide, starch, filter paper, cloth; or any combination of immobilizing agents.

Lipase activity may be detected by Brilliant green, Rhodamine B or Sudan Black in combination with a lipid e.g., olive oil or lard. The screening criteria for identifying variants of parent lipolytic enzymes having improved washing performance may be e.g., EGTA, EDTA, non-ionic or anionic tensides, alkaline pH, or any detergent composition in combination with one of the above detectors of enzymatic activity.

It will be understood that the screening criteria used in the filter assay of the invention may be chosen so as to comply with the desired properties or uses of the enzymes to be screened. For instance, in a screening for lipases of particular use in the paper and pulp industry, it may be relevant to screen for an acid lipase having an increased temperature stability. This may be performed by using a buffer with acidic pH (e.g., pH 4) and/or incubate under higher temperature before or under the assay.

The host cells produced in step (c) may be subjected to further rounds of mutagenesis as defined in steps (a)–(c) above, conveniently by using more stringent selection criteria than employed in a previous mutagenesis treatment.

The host cells selected for in step (c) may be used directly for the production of the variant of the lipolytic enzyme. Alternatively, DNA encoding the variant may be isolated from the host cell and inserted into another suitable host cell, conveniently by use of the procedure described below in the section entitled "Expression of lipase variants," in which suitable host cells are also listed.

Expression of lipase variants

According to the invention, a mutated DNA sequence encoding a variant lipolytic enzyme prepared by methods described above, or any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a variant of the invention or the DNA sequence encoding the parent enzyme during random mutagenesis, may be any vector which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), e.g., as described in WO 93/10249 the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding a variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. The parent lipolytic enzyme may in itself comprise a preregion permitting secretion of the expressed enzyme into the culture medium. If desirable, this preregion may be replaced by a different preregion or signal sequence, convenient accomplished by substitution of the DNA sequences encoding the respective preregions.

The procedures used to ligate the DNA construct of the invention encoding a variant of a parent lipolytic enzyme, the promoter, terminator and other elements, respectively, and to insert them into suitable vectors containing the information necessary for replication, are well known to persons skilled in the art (cf., Sambrook et al., supra).

The cell of the invention either comprising a DNA construct or an expression vector of the invention as defined above is advantageously used as a host cell in the recombinant production of a variant of a parent lipolytic enzyme of the invention. The cell may be transformed with the DNA construct of the invention encoding the variant, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described below in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram-negative bacteria such as *E. coli*. The transformation of the bacteria may for instance be effected by protoplast transformation or by using competent cells in a manner known per se.

The yeast organism may favorably be selected from a species of Saccharomyces or Schizosaccharomyces, e.g., *Saccharomyces cerevisiae*. The filamentous fungus may advantageously belong to a species of Aspergillus, e.g., *Aspergillus oryzae, Aspergillus niger* or *Aspergillus nidulans*. Fungal cells may be transformed by a process involving protoplast formation and transformation of the protoplasts followed by regeneration of the cell wall in a manner known per se. A suitable procedure for transformation of Aspergillus host cells is described in EP 238,023.

The variant of the lipolytic enzyme is produced by a method comprising cultivating a host cell as described above under conditions conducive to the production of the variant and recovering the variant from the cells and/or culture medium.

The medium used to cultivate the cells may be any conventional medium suitable for growing the host cell in question and obtaining expression of the variant of a parent lipolytic enzyme of the invention. Suitable media are available from commercial suppliers or may be prepared according to published recipes (e.g., in catalogues of the American Type Culture Collection).

The variant of the invention secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

Parent Lipase

In the present context, the term "lipolytic enzyme" means an enzyme exhibiting a lipid degrading capability, such as a capability of degrading a triglyceride or a phospholipid. The lipolytic enzyme may, e.g., be a lipase, a phospholipase, an esterase or a cutinase.

Preferably, the parent lipase comprises a trypsin-like catalytic triad including an active serine located in a predominantly hydrophobic, elongated binding pocket of the lipase molecule. The term "trypsin-like" is intended to indicate that the parent lipase comprises a catalytic triad at the active site corresponding to that of trypsin, i.e., the amino acids Ser, His and one of Asp, Glu, Asn or Gln.

The parent lipolytic enzyme may be of any origin. For example, the enzyme may be of mammalian, e.g., pancreatic, gastric, hepatic or lipoprotein lipases, plant, vertebrate or any other source.

It is preferred that the enzyme is of microbial origin in that a number of microbial strains have been found to produce enzymes of particular use for detergent purposes.

More specifically, the parent lipolytic enzyme may be derived from a fungus, i.e., a yeast or a filamentous fungus. For instance, the parent lipolytic enzyme may be derived from a strain of a Humicola sp., e.g., *H. lanuginosa*, a Rhizomucor sp., e.g., *Rh. miehei*, a Rhizopus sp., a Candida sp., a Fusarium sp., e.g., *F. solani pisi*, a Venturia spp., e.g., *V. inaequalis*, a Colletotrichum spp., e.g., *C. gloeosporioides*, or *C. lagenarium*, or a Penicillium spp., e.g., *P. spinulosum* or *P. camembertii*.

Preferably, the parent lipase is a *Humicola lanuginosa* lipase, e.g., the lipase produced by *Humicola lanuginosa* DSM 4109, the cDNA and amino acid sequence of which are shown in SEQ ID NOS:1 and 2, or an analogue of said lipase. Another preferred parent lipase is the *Rhizomiucor miehei* lipase described in EP 305,316. The cDNA and amino acid sequences for this lipase are provided in FIG. 12 in EP 238,023. *H. lanuginosa* lipase and *Rhizomucor miehei* lipase belong to the same group of lipases. Thus, the overall three-dimensional structure of these lipases is very similar and has been shown by X-ray crystallography to be highly homologous (a computer model of the *H. lanuginosa* and the *Rh. miehei* lipase is shown in FIGS. 1A, 1B, 2A and 2B, respectively, from which the similarities between the lipid contact zones of the two lipases are clearly apparent). Also of particular interest as a parent lipolytic enzyme is a lipase derived from a strain of *C. antarctica*.

In the present context, "derived from" means not only an enzyme produced by a strain of the organism in question, but also an enzyme encoded by a DNA sequence isolated from such strain and produced in a host organism in which said DNA sequence has been introduced. Furthermore, this term covers an enzyme which is encoded by a DNA sequence of synthetic and/or cDNA origin and which has the identifying characteristics of the enzyme in question.

In the present context the term "analogue" includes a polypeptide which comprises an amino acid sequence differing from that of the *H. lanuginosa* lipase by one or more amino acid residues, and which is at least 70% homologous with the amino acid sequence of said lipase, (determined as the degree of identity between the two sequences), such as at least 75%, 80%, 90% or 95% homologous, is immunologically cross reactive with said lipase, and/or is encoded by a DNA sequence hybridizing with an oligo nucleotide probe prepared on the basis of the amino acid sequence of said lipase or of a DNA sequence encoding said lipase.

The analogue may be a derivative of the *H. lanuginosa* lipase, e.g., prepared by modifying a DNA sequence encoding the lipase resulting in the addition of one or more amino acid residues to either or both the N- and C-terminal end of the lipase, substitution of one or more amino acid residues at one or more different sites in the amino acid sequence, deletion of one or more amino acid residues at either or both ends of the lipase or at one or more sites in the amino acid sequence, or insertion of one or more amino acid residues at one or more sites in the amino acid sequence. The modification of the DNA sequence may be performed by site-directed or by random mutagenesis or a combination of these techniques in accordance with well-known procedures.

Furthermore, the analogue may be a polypeptide derived from another organism such as one of those mentioned in the section "Background of the Invention" above.

The hybridization of a DNA sequence encoding an analogue of the parent *H. lanuginosa* lipase with the relevant oligonucleotide probe(s) may be carried out under any suitable conditions allowing the DNA sequences to hybridize. For instance, such conditions are hybridization under specified conditions, e.g., involving presoaking in 5×SSC and prehybridizing for 1 h at ~40° C. in a solution of 20% formamide, 5×Denhardt's solution, 50 mM sodium phosphate, pH 6.8, and 50 μg of denatured sonicated calf thymus DNA, followed by hybridization in the same solution supplemented with 100 μM ATP for 18 h at ~40° C., or other methods described by, e.g., Sambrook et al., supra.

The immunological cross-reactivity of an analogue of the *H. lanuginosa* lipase may be assayed using an antibody raised against or reactive with at least one epitope of the purified lipase. The antibody, which may either be monoclonal or polyclonal, may be produced by methods known in the art, e.g., as described by Hudson et al., Practical Immunology, Third edition, Blackwell Scientific Publications, (1989). The immunological cross-reactivity may be determined using assays known in the art, examples of which are Western Blotting or radial immunodiffusion assay, e.g., as described by Hudson et al., supra.

The parent lipolytic enzyme may also be derived from a bacterium. For instance, the DNA sequence encoding the parent lipolytic enzyme may be derived from a strain of Pseudomonas spp., such as *P. cepacia, P. alcaligenes, P. pseudoalcaligens, P. mendocina* (also termed *P. putida*), *P. syringae, P. aeroginosa* or *P. fragi*, a strain of Bacillus spp., e.g., *B. subtilis* or *B. pumilus* or a strain of Streptomyces sp., e.g., *S. scabies*.

The parent bacterial lipolytic enzyme may be a lipase derived from any of the above-mentioned species, e.g., a Pseudomonas lipase as described in EP 218,272, EP 331,376 and EP 407,225, or a cutinase, e.g., as described in WO 88/09367.

Lipid Contact Zone and Surface Loop Structure

Lipolytic enzymes comprise a lipid contact zone which is a surface with increased surface hydrophobicity which interacts with the lipid substrate at or during hydrolysis. The lipid substrate is a conglomerate of single lipid substrate molecules. The lipid contact zone contains a binding area to which a single lipid substrate molecule binds before hydrolysis. This binding area contains an acyl-binding hydrophobic cleft and a so-called hydrolysis pocket, which is situated around the active site Ser, and in which the hydrolysis of the lipid substrate is believed to take place. The lipid contact zone includes one or more protein secondary structure elements, i.e., loop sequences, the amino acid residues of which contact, bind to and/or interact with the substrate during hydrolysis when the lipolytic enzyme is activated.

The lipid contact zone of the lipase produced by *Humicola lanuginosa* DSM 4109 is defined by the amino acid residues at positions 21–25, 36–38, 56–62, 81–98, 110–116, 144–147, 172–174, 199–213 and 248–269.

The lipid contact zone of other lipolytic enzymes is defined by a) calculating the hydrophobic vector of the 3-D molecular structure of the activated enzyme;

b) making a cut perpendicular to the vector through the Cα-atom of the second amino acid residue after the active site serine in the linear sequence;

c) including all residues with at least one atom on that side of the cut to which the vector points; and d) selecting from those residues, those which have at least one atom within 5 Ångström of the surface of the protein.

The hydrophobic vector is calculated from the protein structure by summing up all residue vectors for residues having a surface accessibility (Lee et al., *Mol. Biol.* 55, pp. 379–400 (1971)) of at least 10%. The starting point of the residue vector is defined as the Cα-atom of the residue and its direction is through the mass center of the sidechain. The magnitude of each residue vector is defined as the residues relative free energy of transfer between water and a more hydrophobic solvent (see, e.g., Creighton, Protein, W. Freeman & Co., p. 151 (1984)). The surface accessibility of each residue is calculated using the Connolly program.

Lipases also comprise a surface loop structure, i.e., a lid, which is part of the lipid contact zone. The surface loop structure covers the active serine when the lipase is in inactive form. When the lipase is activated, the surface loop structure shifts to expose the active serine site. The loop structure has a predominantly hydrophobic inner surface facing the binding pocket and a predominantly hydrophilic outer surface. Example of lipases which have a surface loop structure are the *Rhizomucor miehei* lipase described by Brady et al., supra, and human pancreatic lipase described in Winkler et al., *Nature* 343, pp. 771–74 (1990).

The surface loop structure of the lipase produced by *Humicola lanuginosa* DSM 4109 is defined by amino acid residues at positions 82–96.

Variants of Lipolytic Enzymes

In describing variants of lipolytic enzymes according to the invention, the following nomenclature is used for ease of reference:

Original amino acid:position:substituted amino acid.

According to this nomenclature, the substitution of aspartic acid for tryptophan in position 96 is shown as Asp 96 Trp or D96W.

Multiple mutations are separated by pluses, e.g.,:

Asp 96 Leu+Leu 206 Val or D96L+L206V representing mutations in positions 96 and 206 substituting aspartic acid and leucine for leucine and valine, respectively.

The lipase variants are mostly defined by use of the conventional one-letter amino acid code. The numbering of the amino acid residues refers to the amino acid sequence of the mature lipase.

Furthermore, when a position suitable for modification is identified herein without any specific modification being suggested, it is to be understood that any amino acid residue may be substituted for the amino acid residue present in the position. Thus, for instance, when a modification of an aspartic acid in position 96 is mentioned, but not specified, it is to be understood that the aspartic acid may be deleted or substituted for any other amino acid, i.e., any one of R,N,A,C,Q,E,G,H,I,L,K,M,F,P,S,T,W,Y,V, or a further amino acid residue inserted at that position.

Finally, when a mutation of the parent *H. lanuginosa* lipase is identified herein, it is intended to be understood as including a similar mutation of an analogue of said lipase.

In a first embodiment, the present invention relates to lipase variants wherein the electrostatic charge and/or hydrophobicity of the lipid contact zone of a parent lipase is changed by deleting or substituting one or more negatively charged amino acid residues by neutral or positively charged amino acid residue(s), and/or by substituting one or more neutral amino acid residues by positively charged amino acid residue(s), and/or by deleting or substituting one or more hydrophilic amino acid residues by hydrophobic amino acid residue(s). In this embodiment, the lipase variant is preferably one in which one or more glutamic acid or aspartic acid residues of the lipid contact zone are substituted by glutamine, asparagine, alanine, leucine, valine, serine, threonine, lysine, or arginine.

Preferably, in this embodiment, the lipase variant is of the parent lipase produced by *Rhizomucor miehei*, wherein one or more negatively charged amino acid residues are substituted by one or more positively charged or neutral amino acid residues as follows:

D61N, K, R, A, V, L, S, T;

D91N, K, R, A, V, L, S, T;

D113N, K, R, A, V, L, S, T;

E201Q, K, R, A, V, L, S, T;

D226N, K, R, A, V, L, S, T;

D243N, K, R, A, V, L, S, T; or

D256N, K, R, A, V, L, S, T.

Also preferred in this embodiment are variants of the lipase produced by *H. lanuginosa* strain DSM 4109 (SEQ ID NO:2). Specifically, lipase variants of this parent lipase include substitutions of one or more negatively charged amino acid residues by one or more neutral or positively charged amino acid residues as follows:

D27A, Q, N, T, S, K, R, L, V;

E56Q, K, R, A, N, T, S, L, V;

E57A, Q, N, T, S, K, R, L, V;

D62A, Q, N, T, S, K, R, L, V;

E87Q, K, R, A, N, T, S, L, V;

D96N, K, R, A, Q, T, S, L, V;

E99A, Q, N, T, S, K, R, L, V;

D111N, K, R, A, Q, T, S, L, V;

E210Q, K, R, A, N, T, S, L, V;

E219A, Q, N, T, S, K, R, L, V;

E234A, Q, N, T, S, K, R, L, V;

E239A, Q, N, T, S, K, R, L, V;

D242N, K, R, A, Q, T, S, L, V; or

D254N, K, R, A, Q, T, S, L, V.

Particularly preferred substitutions of *H. lanuginosa* lipase according to the invention are:

E87Q+E210Q+D242N+D254N;
E87Q+E210Q+D254N;
E87Q+D96N+D254N; and
R209A+E210A.

Alternatively, one or more amino acid residues of the lipid contact zone of *H. lanuginosa* lipase may be substituted by one or more positively charged amino acid residues as follows:

S85K, R;
N88K, R;
N92K, R;
I202K, R;
V203K, R;
L206K, R;
T226K, R;
L227K, R;
I255K, R;
L259K, R; or
T267K, R.

In a second embodiment, the present invention relates to lipase variants wherein one or more amino acid residues are substituted, deleted, or inserted in the lipid contact zone in order to change the surface conformation of said lipid contact zone. The purpose of such a surface modification of the lipase molecule is to provide improved accessibility of the active site of the lipase to a lipid substrate. In this embodiment, preferably, one or more amino acid residues are substituted by one or more other, less bulky amino acid residues. The purpose of such modification is to expose the active site of the lipase and, therefore, make it more available for contact with the substrate. In particular, the less bulky amino acid residues may be selected from valine, threonine, serine, glycine or alanine.

In this embodiment, when the parent lipase is *Rhizomucor miehei*, preferred variants include the following variants:

I204V, A, T, S, G;
L208V, A, T, S, G;
F213V, A, T, S, G; or
I254V, A, T, S, G.

Other preferred variants of *Rhizomucor miehei* lipase include the deletion of one or more amino acid residues at one or more of the following positions of: 82–113, 211–215, 235–243, 245–269 or 264–269. Specific examples of suitable deletions and substitutions are as follows:

C22T+N264*+T265*+G266*+L267*+C268*+T269*;
F213*+F215*;
D238*+L239*+E240*+D243*; or
S247*+F251*+T252*.

In this embodiment, when the parent lipase is *Humicola lanuginosa* lipase, preferred variants include the following substitutions:

I202V, A, T, S, G;
L206V, A, T, S, G;
F211V, A, T, S, G, I; or
I255V, A, T, S, G.

Other preferred variants of *H. lanuginosa* lipase include the deletion of one or more amino acid residues at one or more of the following positions of: 84–112, 209–213, 238–245, 247–254 or 264–269. Specific examples of suitable deletions and substitutions are as follows:

C22T+L264*+I265*+G266*+T267*+C268*+L269*;
R209*+E210*;
F211*+Y213*;
E239*+I241*+D242*; and
N247*+D254*.

In a third embodiment, the present invention relates to lipase variants of a parent lipase comprising a surface loop structure, wherein one or more amino acid residues in the surface loop structure and/or the lipid contact zone near the active serine residue are substituted, deleted or inserted. In this embodiment, preferably, at least two amino acid residues of the surface loop structure are substituted by cysteine, wherein the two cysteine residues are positioned to form a disulphide bond. This will cause the surface loop structure to shift and become more open so that the active serine residue becomes more accessible to the substrate.

In this embodiment, when the parent lipase is *Rhizomucor miehei* lipase, preferred variants include the following substitutions:

Y60C+R78C;
Y60C+N87C;
D61C+S84C;
D61C+R86C;
D61C+N87C; or
A90C+S114C.

Other preferred variants of *Rhizomucor miehei* lipase may be obtained by substituting one or more hydrophilic amino acid residues by one or more less hydrophilic amino acid residues of the binding pocket in which the catalytic triad, including the active serine, is located, as follows:

F94L, T, K;
I204V, A, T, S, G;
L208V, A, T, S, G;
F213V, A, T, S, G;
I254V, A, T, S, G;
L255V, A, T, S, G;
L258V, A, T, S, G; or
L267V, A, T, S, G.

Furthermore, the amino acid substitutions of *Rhizomucor miehei* lipase in the surface loop structure and/or lipid contact zone may be combined as follows:

I204T+L255T+L267T; or
L208T+I254T+L258T.

However, preferably, tryptophan at position 88 of *Rhizomucor miehei* lipase, i.e., W88, is conserved.

In this embodiment, when the parent lipase is *Humicola lanuginosa* lipase, preferred variants include the following substitutions:

G61C+N88C;
G61C+E87C;
D62C+E87C;
D62C+S85C;
D62C+N88C; or
G91C+S116C.

However, preferably, tryptophan at position 89 of *Humicola lanuginosa* lipase, i.e., W89, is conserved.

Alternatively, one or more hydrophilic amino acid residues of the lipid contact zone of the *Humicola lanuginosa* lipase may be substituted by one or more less hydrophilic amino acid residues, wherein the hydrophilic amino acid residues are located in the binding pocket in which the catalytic triad, including the active serine, is located, as follows:

I86V, T, S, A, G;
I90V, T, S, A, G;
L93V, T, S, A, G;
F95L, T, K;
I202V, T, S, A, G;
L206V, T, S, A, G;
F211L, T, K;
I255V, T, S, A, G; or
L259V, T, S, A, G.

Preferred among these lipase variants are the following:
I86T;
I90T;
F95K;
L206T;
L206T+I255T+L259T;
I255T; and
L259T.

In a fourth embodiment, the present invention relates to lipase variants wherein a non-aromatic amino acid residue of the lipid contact zone is substituted with an aromatic amino acid residue. An aromatic amino acid residue is defined as tyrosine, tryptophan or phenylalanine, and a non-aromatic amino acid residue is defined as an amino acid residue other than tyrosine, tryptophan and phenylalanine. Preferably, the non-aromatic amino acid residue is a glutamic acid or an aspartic acid residue.

In this embodiment, when the parent lipase is *Humicola lanuginosa* lipase, preferred variants include substitutions of the aromatic amino acid residue located in position 96. Further specific variants of *H. lanuginosa* lipase comprises one or more amino acid residues substituted as follows:

E56H, P, M, W, Y, F, I, G, C, V;
D96H, E, P, M, W, Y, F, I, G, C, V;
L206K, R, N, D, C, Q, E, H, I, M, F, P, W, Y; and
L259N, D, C, Q, E, H, I, M, F, P, W, Y.

A particularly interesting effect may also be obtained when the lipase variant of the invention comprises more than one substitution, preferably two substitutions. For instance, the following variants of *H. lanuginosa* lipase have been found to be of interest:

E56Q+L259I+L206V;
D96L+L206S;
D96L+L206V;
D96L+L259I+L206V;
D96W+D102N;
D96W+E210N; and
D254K+L259I.

In a fifth embodiment, the present invention relates to variants produced by random mutagenesis.

In this embodiment, when the parent lipolytic enzyme is the *H. lanuginosa* lipase obtainable from strain DSM 4109 or an analogue thereof as defined above, it is preferred that the variant comprises a mutation in at least one of the following positions: S58, T64, S83, N94, K98, I100, A121, E129, D167, R205, K237, I252, P256 or G263.

Other variants of the *H. lanuginosa* lipase include the substitution of the amino acid residue L264 by an amino acid different from leucine, i.e., any one of R, N, A, C, Q, E, G, H, I, K, M, F, P, S, T, W, Y, V, D.

Preferably, the variant according to this embodiment of the invention comprises at least one of the following mutations K46R, E57G, G61S, S83T, S58F, D62C, T64R, I90F, G91A, N92H, N94I, N94K, L97M, K98I, I100V, D102K, A121V, E129K, D167G, R205K, E210W, K237M, N259W, I252L, D254W, P256T, G263A, L264Q or T267W.

Preferably, the variant according to this aspect of the invention comprises at least one of the following mutations S83T, N94K, A121V, D167G, R205K.

Additional variants of this embodiment of the invention include at least one of the following mutations:
N94K+D96A
S83T+N94K+D96N
E87K+D96V
E87K+G91A+D96A
N94K+F95L+D96H
A121V+R205K+E210Q
F95C+D96N
G91S+L93V+F95C
E87K+G91A+D96R+I100V
E87K+G91A
S83T+E87K+Q249R
S83T+E87K+W89G+G91A+N94K+D96V
N73D+S85T+E87K+G91A+N94K+D96A
E87K+G91A+L93I+N94K+D96A
D167G+E210V
N73D+E87K+G91A+N94I+D96G
S83T+E87K+G91A+N92H+N94K+D96M
E210W
E56T+D57L+I90F+D96L+E99K
E56R+D57L+V60M+D62N+S83T+D96P+D102E
D57G+N94K+D96L+L97M
E87K+G91A+D96R+I100V+E129K+K237M+I252L+
    P256T+G263A+L264Q
E56R+D57G+S58F+D62C+T64R+E87G+G91A+F95L+
    D96P+K98I+K237M
K46R+E56R+G61S
D102K
D167G
N73D+E87K+G91A+N94I+D96G
E210V
E210W
N251W+D254W+T267W
S83T+E87K+G91A+N92H+N94K+D96M
E56R+I90F+D96L+E99K
D57G+N94K+D96L+L97M It should be noted that any of the modifications of the amino acid sequence disclosed above may be combined with any of the other modifications.

Lipase variants of other parent lipases by similar substitutions as those described for *H. lanuginosa* and *Rh. miehei* lipases are also within the scope of the present invention. Similar substitutions means amino acid substitutions of other lipases, which are performed in similar positions to those identified above for these lipases. Similar positions may be identified by comparing the three-dimensional structure of the lipase in question with those of the *H. lanuginosa* and *Rh. miehei* lipases. The three-dimensional structure of other parent lipases either are known or may be elucidated by conventional methods, e.g., involving X-ray analysis.

Detergent Additives and Compositions

The present invention further relates to detergent additives comprising a lipase variant of the invention preferably in the form of a non-dusting granulate, stabilized liquid or protected enzyme, as well as to detergent compositions comprising a lipase variant of the invention. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molecular weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono-, di- and triglycerides of fatty acids. Examples of film-forming coating materials suitable for application by fluid bed techniques are given in patent GB 1,483,591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g., as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. Examples of non-ionic surfactants include an alcohol ethoxylate, examples of anionic surfactants include LAS, alkyl sulphate, alcohol ethoxy sulphate and the like.

The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), a commercially available example of which is Dobanol®, carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g., as described in WO 92/06154).

The detergent composition may additionally comprise one or more other enzymes, such as an amylase, a pullulanase, a cutinase, a protease, a cellulase, a peroxidase, an oxidase (e.g., a laccase), and/or another lipase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e., essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g., a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g., 7–11.

Particular forms of detergent compositions within the scope of the invention include:

(1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g., $C_{12-18}$ alcohol, 1-2 EO) or alkyl sulfate (e.g., $C_{16-18}$) | 1–4% |
| Alcohol ethoxylate (e.g., $C_{14-15}$ alcohol, 7 EO) | 5–9% |
| Sodium carbonate (as $Na_2CO_3$) | 14–20% |
| Soluble silicate (as $Na_2O,2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g., $C_{12-18}$ alcohol, 1-2 EO or alkyl sulfate (e.g., $C_{16-18}$) | 1–3% |
| Alcohol ethoxylate (e.g., $C_{14-15}$ alcohol, 7 EO) | 5–9% |
| Sodium carbonate (as $NaCO_3$) | 15–21% |
| Soluble silicate (as $Na_2O,2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g., maleic/acrylic acid copolymer, PVP, PEG) | 1–6% |
| Enzymes (calculated as pure enzyme protein) | 0.0001–0.1% |
| Minor ingredients (e.g., suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g., $C_{12-15}$ alcohol, 7 EO) | 7–14% |
| Soap as fatty acid (e.g., $C_{16-22}$ fatty acid) | 1–3% |
| Sodium carbonate (as $Na_2CO_3$) | 10–17% |
| Soluble silicate (as $Na_2O,2SiO_2$) | 3–9% |
| Zeolite (as $NaAlSiO_4$) | 23–33% |
| Sodium sulfate (as $Na_2SO_4$) | 0–4% |
| Sodium perborate (as $NaBO_3.H_2O$) | 8–16% |
| TAED | 2–8% |
| Phosphonate (e.g., EDTMPA) | 0–1% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g., $C_{12-15}$ alcohol, 7 EO) | 10–25% |
| Sodium carbonate (as $Na_2CO_3$) | 14–22% |
| Soluble silicate (as $Na_2O,2SiO_2$) | 1–5% |
| Zeolite (as $NaAlSiO_4$) | 25–35% |
| Sodium sulfate (as $Na_2SO_4$) | 0–10% |

| | |
|---|---|
| Carboxymethylcellulose | 0–2% |
| Polymers (e.g., maleic/acrylic acid copolymer, PVP, PEG) | 1–3% |
| Enzymes (calculated as pure enzyme protein) | 0.0001–0.1% |
| Minor ingredients (e.g., suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO or $C_{12-15}$ alcohol, 5 EO) | 12–18% |
| Soap as fatty acid (e.g., oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g., PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g., dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g., $C_{21-15}$ alcohol, 7 EO, or $C_{12-15}$ alcohol, 5 EO) | 3–9% |
| Soap as fatty acid (e.g., oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g., PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g., dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O,2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g., maleic/acrylic acid copolymer, PEG) | 1–5% |
| Enzymes (calculated as pure enzyme protein) | 0.0001–0.1% |
| Minor ingredients (e.g., optical brighteners, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O,2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g., PVP, maleic/acrylic acid copolymer, PEG) | 1–5% |
| Enzymes (calculated as pure enzyme protein) | 0.000–0.1% |
| Minor ingredients (e.g., suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g., NOBS or TAED) | 1–5% |
| Carboxymethylcellulose | 0–2% |
| Polymers (e.g., polycarboxylate or PEG) | 1–5% |
| Enzymes (calculated as pure enzyme protein) | 0.0001–0.1% |
| Minor ingredients (e.g., optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g., $C_{12-15}$ alcohol, 2-3 EO) | 8–15% |
| Alcohol ethoxylate (e.g., $C_{12-15}$ alcohol, 7 EO, or $C_{12-15}$ alcohol, 5 EO) | 3–9% |
| Soap as fatty acid (e.g., lauric acid) | 0–3% |
| Aminoethanol | 1–5% |
| Sodium citrate | 5–10% |
| Hydrotrope (e.g., sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g., polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g., $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g., maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g., hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g., alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g., perfume, optical brighteners) | 0–3% |

13) Detergent formulations as described in 1)–12) wherein all or part of the linear alkylbenzenesulfonate is replaced by ($C_{12}$–$C_{18}$) alkyl sulfate.

14) A detergent composition formulated as a granulate having a bulk density of at least 600 g/l composing

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g., SK56 from Hoechst) | 10–20% |
| Sodium carbonate (as $Na_2CO_3$) | 3–12% |
| Soluble silicate (as $Na_2O, 2SiO_2$) | 0–6% |
| Sodium citrate | 4–8% |
| Sodium percarbonate | 13–22% |
| TAED | 3–8% |
| Polymers (e.g., polycarboxylates and PVP = | 0–5% |
| Enzymes (calculated as pure enzyme protein) | 0.0001–0.1% |
| Minor ingredients (e.g., optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O, 2SiO_2$) | 0–4% |

-continued

| | |
|---|---|
| Sodium percarbonate | 13–22% |
| TAED | 1–8% |
| Carboxymethyl cellulose | 0–3% |
| Polymers (e.g., polycarboxylates and PVP) | 0–3% |
| Enzymes (calculated as pure enzyme protein) | 0.0001–0.1% |
| Minor ingredients (e.g., optical brightener, phosphonate, perfume) | 0–3% |

16) Detergent formulations as described in 1)–15) which contain a stabilized or encapsulated peracid, either as an additional component or as a substitute for already specified bleach systems.
17) Detergent compositions as described in 1), 3), 7), 9) and 12) wherein perborate is replaced by percarbonate.
18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, pp. 637–39 (1994).
19) Detergent compositions formulated as a nonaqueous detergent liquid comprising a liquid nonionic surfactant such as, e.g., linear alkoxylated primary alcohol, a builder system (e.g., phosphate), enzyme and alkali. The detergent may also comprise anionic surfactant and/or a bleach system.

The lipase variant of the invention may be incorporated in concentrations conventionally employed in detergents. It is at present contemplated that, in the detergent composition of the invention, the lipase variant may be added in an amount corresponding to 0.001–100 mg of enzyme per liter of wash liquor.

Dishwashing Composition

The lipase variant may also be used as an ingredient in dishwashing detergent compositions. The dishwashing detergent composition comprises a surfactant which may be anionic, non-ionic, cationic, amphoteric or a mixture of these types. The detergent will contain 0–90% of non-ionic surfactant such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1–90% of detergent builders.

Examples of phosphorus-containing inorganic alkaline detergent builders include the water-soluble salts especially alkali metal pyrophosphates, orthophosphates, polyphosphates, and phosphonates. Examples of non-phosphorus-containing inorganic builders include water-soluble alkali metal carbonates, borates and silicates as well as the various types of water-insoluble crystalline or amorphous alumino silicates of which zeolites are the best-known representatives.

Examples of suitable organic builders include the alkali metal, ammonium and substituted ammonium, citrates, succinates, malonates, fatty acid sulphonates, carboxymetoxy succinates, ammonium polyacetates, carboxylates, polycarboxylates, aminopolycarboxylates, polyacetyl carboxylates and polyhydroxsulphonates.

Other suitable organic builders include the higher molecular weight polymers and co-polymers known to have builder properties, e.g., appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches are preferred, e.g., in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g., a polyol such as, e.g., propylene glycol, a sugar or a sugar alcohol, lactic acid, boric acid, or a boric acid derivative, e.g., an aromatic borate ester.

The dishwashing detergent composition may also comprise other enzymes, in particular an amylase, a protease and/or a cellulase.

The dishwashing detergent composition of the invention may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners and perfumes.

Finally, the variant of the invention may be used in conventional dishwashing detergents, e.g., any of the detergents described in any of the following patent publications: EP 551,670, EP 533,239, WO 93/03129, EP 507,404, GB 2,247,025, EP 414,285, GB 2,234,980, EP 408,278, GB 2,228,945, GB 2,228,944, EP 387,063, EP 385,521, EP 373,851, EP 364,260, EP 349,314, EP 331,370, EP 318,279, EP 318,204, GB 2,204,319, EP 266,904, EP 530,870, CA 2,006,687, EP 481,547, EP 337,760, WO 93/14183, WO 93/06202, WO 93/05132, WO 92/19707, WO 92/09680, WO 92/08777, WO 92/06161, WO 92/06157, WO 92/06156, WO 91/13959, EP 399,752, and U.S. Pat. Nos. 4,941,988, 4,908,148, 5,141,664, 5,213,706 and 5,223,179.

Softening composition

Furthermore, the lipase variants of the invention may be used in softening compositions:

The lipase variant may be used in fabric softeners, e.g., as described in Surfactant and Consumer Products, Ed. by Falbe, pp. 295–96 (1987); Tenside Surfactants Detergents 30(6), pp. 394–99 (1993); JAOCS 61(2), pp. 367–76 (1984); EP 517,762; EP 123,400; WO 92/19714; WO 93/19147; EP 494,769; EP 544,493; EP 543,562; EP 568,297; EP 570,237 and U.S. Pat. Nos. 5,082,578 and 5,235,082.

The present invention is further illustrated in the following examples which are not in any way intended to limit the scope of the invention as claimed.

MATERIALS AND METHODS

Figure 8:
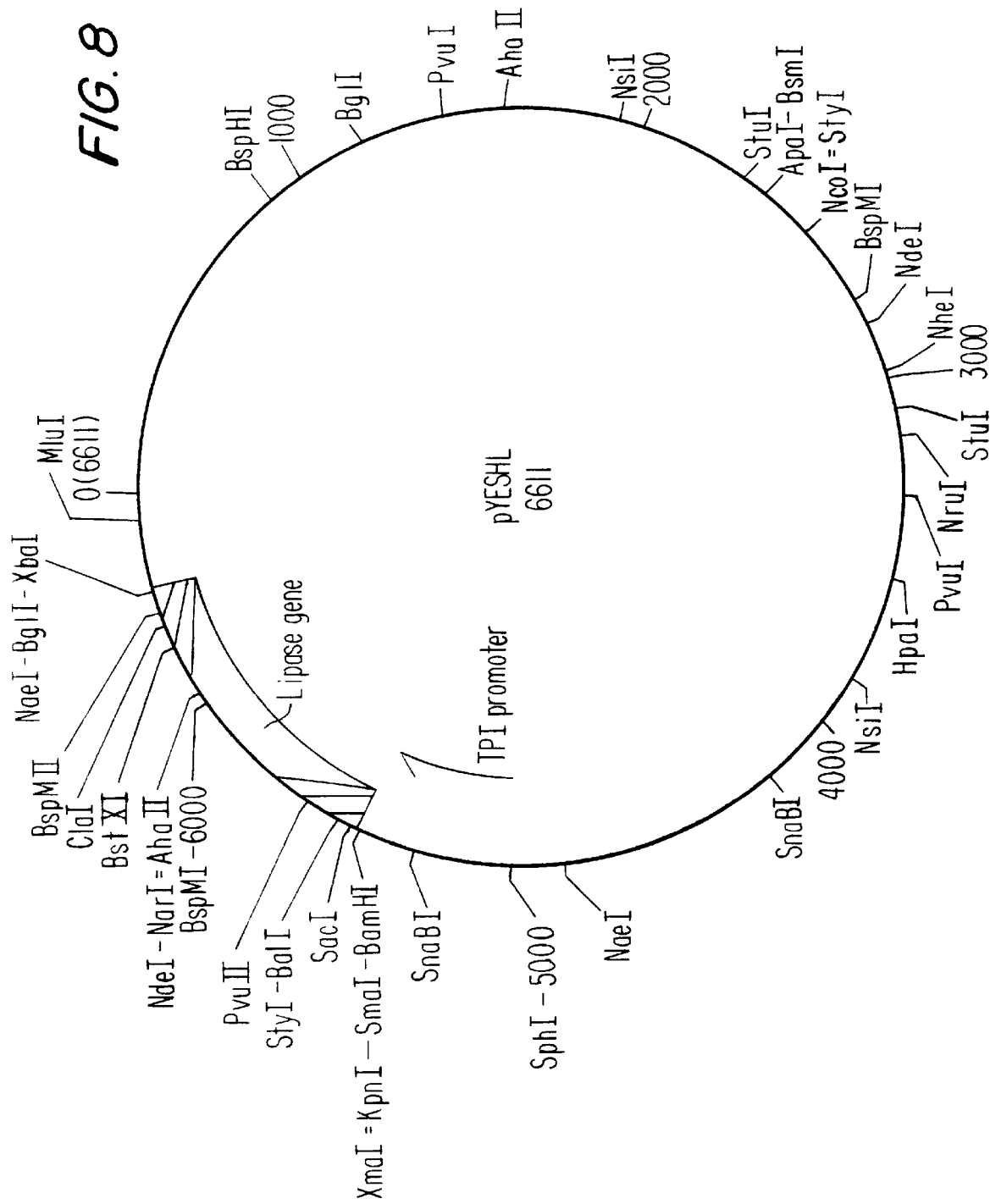
FIG. 8 shows a restriction map of pYESHL.

*Humicola lanuginosa* DSM 4109 available from the Deutsche Sammlung von Mikroorganismen und Zellkulturen GmbH, Mascheroderweg 1b, D-3300 Braunschweig, Federal Republic of Germany.

pYESHL is a yeast/*E. coli* shuttle vector that expresses and secretes a low level of the *H. lanuginosa* lipase in yeast. More specifically pYESHL is a derivative of pYES2 (purchased from Invitrogen Corp., UK) in which the GAL1 promoter was excised and the *Humicola lanuginosa* lipase gene and the TPI (triose phosphate isomerase) promoter from *S. cerevisiae* (Alber et al., *J. Mol. Appl. Genet.* 1, 419–34 (1982)) were cloned between the SphI and XbaI sites. A restriction map of pYESHL is shown in FIG. 8.

Expression of *H. lanuginosa* lipase in Aspergillus oryzae

Cloning of *Humicola lanuginosa* lipase and *Rhizomucor miehei* lipase is described in EP 305,216 and EP 238,023, respectively. These patent applications also describe expression and characterization of the two lipases in *Aspergillus oryzae*. The two expression plasmids used are named p960 (carrying the *H. lanuginosa* lipase gene) and p787 (carrying the *R. miehei* lipase gene).

Figure 6:
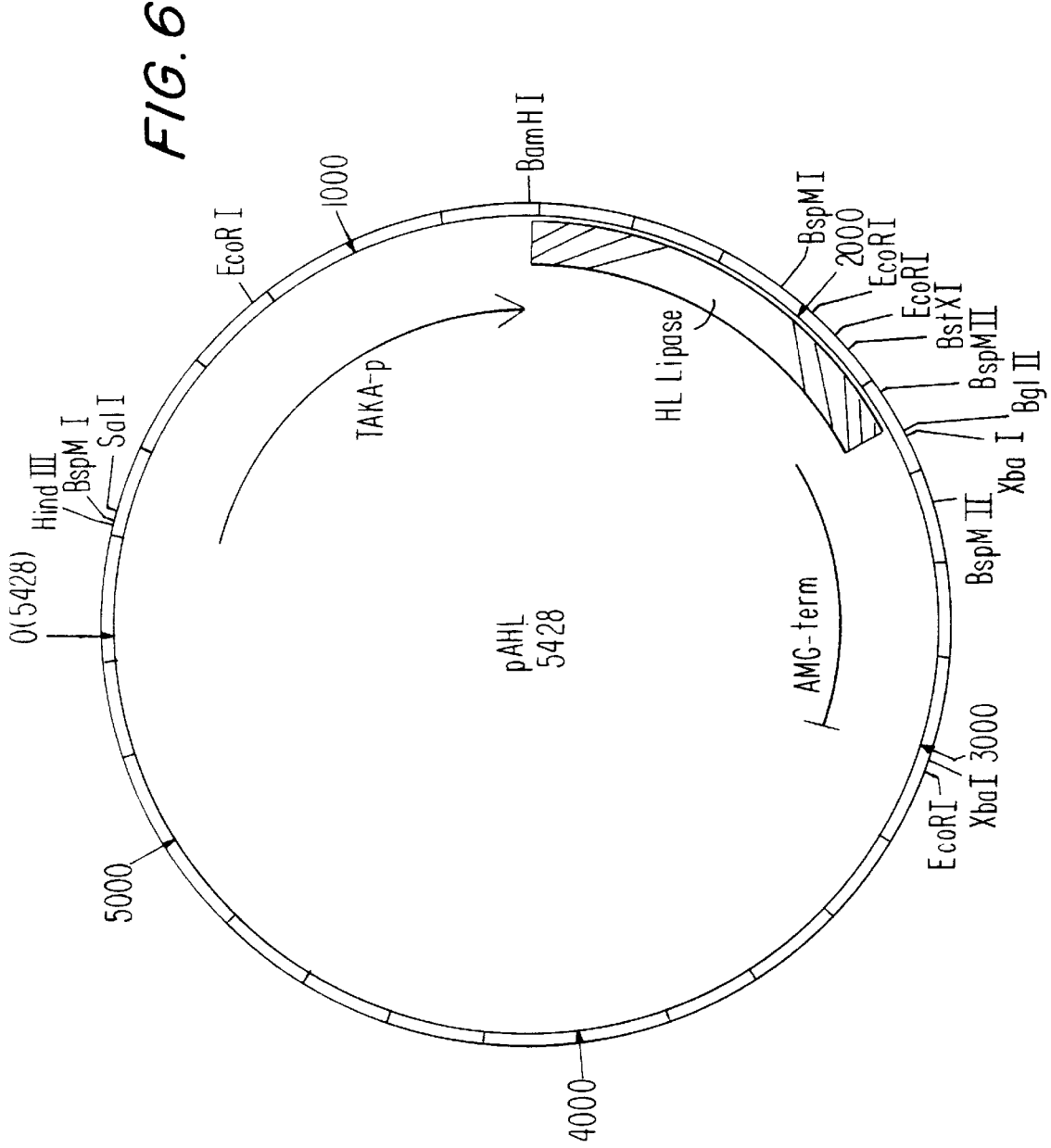
FIG. 6 shows a restriction map of plasmid pAHL.
Figure 7:
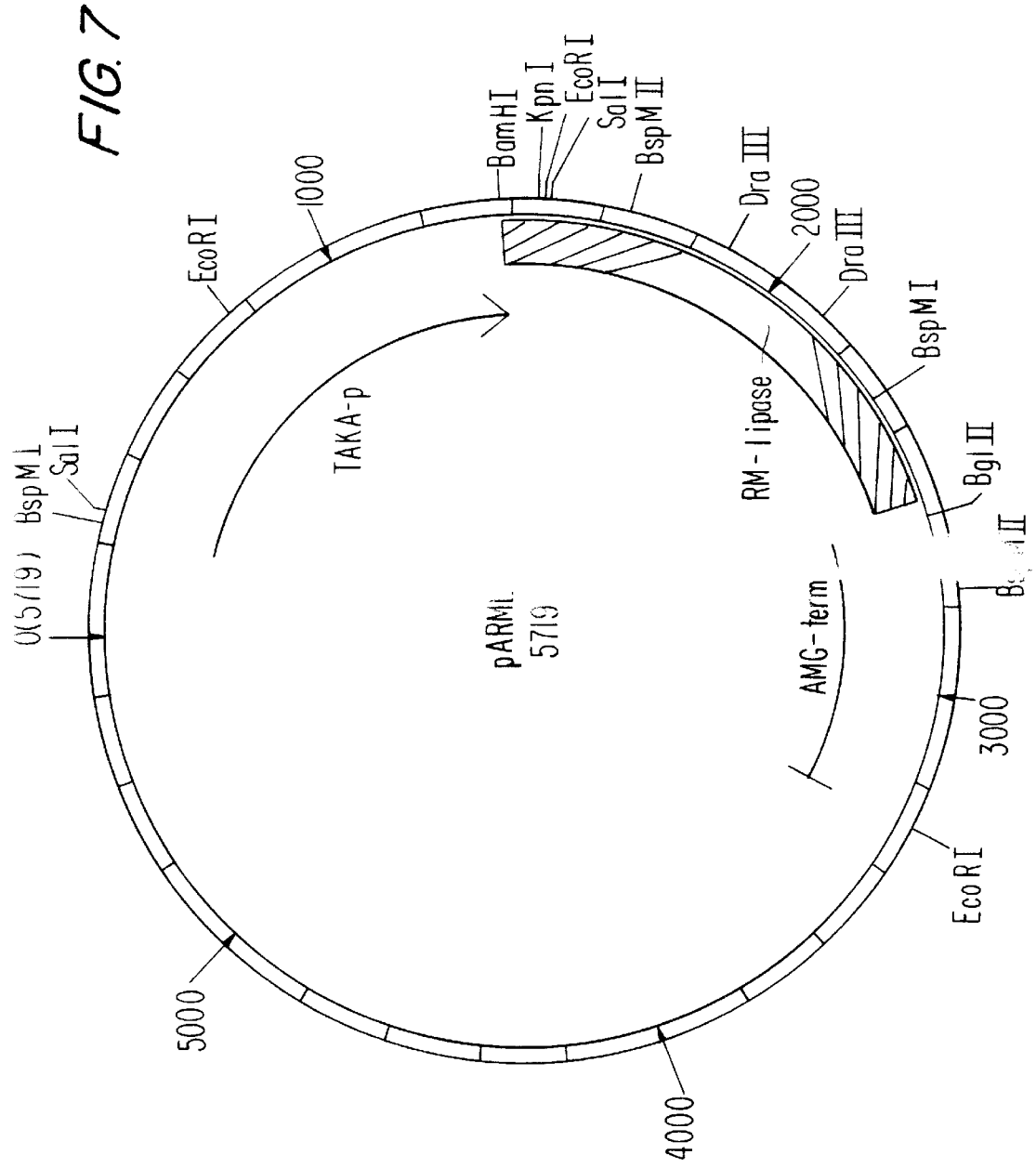
FIG. 7 shows a restriction map of plasmid pARML.

The expression plasmids used in this application are identical to p787 and p960, except for minor modifications immediately 3' to the lipase coding regions. The modifications were made in the following way: p960 was digested with NruI and BamHI restriction enzymes. Between these two sites the BamHI/NheI fragment from plasmid pBR322, in which the NheI fragment was filled in with Klenow polymerase, was cloned, thereby creating plasmid pAO1 (FIG. 5) which contains unique BamHI and NheI sites. Between these unique sites BamHI/XbaI fragments from p960 and p787 were cloned to give pAHL (FIG. 6) and pARML (FIG. 7), respectively.

Site-directed in vitro mutagenesis of a lipase gene

Three different approaches were used for introducing mutations into the lipase genes.

One method employed was oligonucleotide site-directed mutagenesis which is described by Zoller et al., DNA 3(6), pp. 479–88 (1984). The method is described briefly below and thoroughly in Example 1.

Isolated from the expression plasmid, the lipase gene of interest is inserted into a circular M13 bacteriophage vector. To the single-stranded genome, a chemically synthesized complementary DNA-strand is annealed. This DNA-strand contains the mutation to be introduced flanked by sequences complementary to lipase sequences on the circular DNA. In vitro, the primer is then extended in the entire length of the circular genome biochemically using Klenow polymerase. When transformed in *E. coli*, the heteroduplex will give rise to double-stranded DNA with the desired sequence from which a fragment can be isolated and re-inserted into the expression plasmid.

Another method employed is described in Nelson et al., *Analytical Biochemistry* 180, pp. 147–51 (1989). It involves the 3-step generation of a PCR fragment containing the desired mutation introduced by using a chemically synthesized DNA-strand as one of the primers in the PCR-reactions. From the PCR-generated fragment, a DNA fragment carrying the mutation can be isolated by cleavage with restriction enzymes and re-inserted into the expression plasmid. This method is thoroughly described in Example 3. This method is further outlined in FIGS. 3 and 4.

In a further method, usually termed "cassette mutagenesis", a segment between two restriction sites of the lipase-encoding region is replaced by a synthetic DNA fragment carrying the desired mutation.

Low calcium filter assay

Procedure

1) Provide SC Ura replica plates (useful for selecting strains carrying the expression vector) with a first protein binding filter (Nylon membrane) and a second low protein binding filter (Cellulose acetate) on the top.
2) Spread yeast cells containing a parent lipase gene or a mutated lipase gene on the double filter and incubate for 2 or 3 days at 30° C.
3) Keep the colonies on the top filter by transferring the topfilter to a new plate.
4) Remove the protein binding filter to an empty petri dish.
5) Pour an agarose solution comprising an olive oil emulsion (2% P.V.A.:Olive oil=3:1), Brilliant green (indicator, 0.004%), 100 mM tris buffer pH9 and EGTA (final concentration 5mM) on the bottom filter so as to identify colonies expressing lipase activity in the form of blue-green spots.
6) Identify colonies found in step 5) having a reduced dependency for calcium as compared to the parent lipase.

Dobanol™ 25-7 filter assay

The screening for an improved tolerance towards a detergent component is performed by use of a filter assay corresponding to that described above except for the fact that the solution defined in 5) further comprises 0.02% Dobanol™ 25-7.

Construction of random mutagenized libraries a) Using an entire lipase coding gene The plasmid pYESHL is treated with 12M formic acid for 20 min. at room temperature. The resulting lipase encoding gene is amplified from the formic acid treated plasmid using PCR under mutagenic conditions (0.5 mM $MnCl_2$ and ⅕ the normal amount of ATP, see e.g., Leung et al., supra).

This treatment is expected to give a broad range of mutations since formic acid gives mainly transversions and PCR generated mutations mainly transitions.

The resulting PCR fragments are cloned either by double recombination (Muhlrad et al., *Yeast* 8, pp. 79–82 (1992)) in vivo into the shuttle vector or digestion and ligation into the shuttle vector and transformation of *E. coli*.

Eight randomly picked clones have been sequenced and were foun to contain 2–3 mutations in average—both transversion and transitions.

By use of this method seven libraries have been made containing from 10,000 to 140,000 clones.

b) Performing localized random mutagenesis

A mutagenic primer (oligonucleotide) is synthesized which corresponds to the part of the DNA sequence to be mutagenized except for the nucleotide(s) corresponding to amino acid codon(s) to be mutagenized.

Subsequently, the resulting mutagenic primer is used in a PCR reaction with a suitable opposite primer. The resulting PCR fragment is purified and digested and cloned into the shuttle vector. Alternatively and if necessary, the resulting PCR fragment is used in a second PCR reaction as a primer with a second suitable opposite primer so as to allow digestion and cloning of the mutagenized region into the shuttle vector. The PCR reactions are performed under normal conditions.

DNA sequencing was performed by using applied Biosystems ABI DNA sequence model 373A according to the protocol in the ABI Dye Terminator Cycle Sequencing kit.

EXAMPLES

Example 1

Construction of a Plasmid Expressing the D96L Variant of *Humicola lanuginosa* Lipase Isolation of the lipase gene The expression plasmid p960 contains the coding region for *Humicola lanuginosa* lipase on a BamHI/XbaI restriction fragment. The BamHI/XbaI fragment was isolated as follows: The expression plasmid was incubated with the restriction endonucleases BamHI and XbaI. The conditions were: 5 µg plasmid, 10 units of BamHI, 10 units of XbaI, 100 mM NaCl, 50 mM Tris-HCl, pH 7.5, 10 mM MgCl$_2$ and 1 mM DTT in 50 μl volume. The temperature was 37° C. and the reaction time 2 hours. The two fragments were separated on a 1% agarose gel and the desired fragment was isolated from the gel.

Ligation to the vector M13mp18

The bacteriophage vector M13mp18 on its double-stranded, replicative form was digested with BamHI and XbaI under conditions as described above. The isolated restriction fragment was ligated to the digested bacteriophage vector in the following reaction mixture: Fragment 0.2 μg, vector 0.02 μg, 50 mM Tris-HCl, pH 7.4, 10 mM MgCl$_2$, 10 mM DTT and 1 mM ATP in a 20 μl volume at 16° C. for 3 hours. 5 μl of this mixture was transformed into the E. coli strain JM101. The presence of fragment in the vector was identified by restriction enzyme analysis on double-stranded M13-DNA isolated from the transformants.

Isolation of single-stranded (ss) DNA (template)

From the transformant described above, ss-DNA was isolated according to a method described by Messing, Gene 19, pp. 269–76 (1982).

5' phosphorylation of the mutagenisation primer

The mutagenisation primer with the sequence 5'-TTTCTTTCAACAAGAAGTTAAGA-3' (SEQ ID NO:3) was phosphorylated at the 5' end in a 30 μl reaction mixture containing 70 mM Tris-HCl, pH 7.0, 10 mM MgCl$_2$, 5 mM DTT, 1 mM ATP, 100 pmol oligonucleotide and 3.6 units of T4 polynucleotide kinase. The reaction reaction was carried out for 30 min. at 37° C. Then, the enzyme was inactivated by incubating the mixture for 10 min. at 65° C.

Annealing of template and phosphorylated mutagenisation primer

Annealing of template and primer was carried out in a 10 μl volume containing 0.5 pmol template, 5 pmol primer, 20 mM Tris-HCl, pH 7.5, 10 mM MgCl$_2$ 50 mM NaCl and 1 mM DTT by heating for 10 min. at 65° C. and cooling afterwards to 0° C.

Extension/ligation reaction

To the reaction mixture above, 10 μl of the following mixture was added: 0.3 mM dATP, 0.3 mM dCTP, 0.3 mM dGTP, 0.3 mM TTP, 1 mM ATP, 20 mM Tris-HCl, pH 7.5, 10 mM MgCl$_2$, 10 mM DTT, 3 units of T4 DNA ligase and 2.5 units of Klenow polymerase. Then, the reaction was carried out for 16 hours at 16° C.

Transformation of JM101

The reaction mixture above was transformed in different dilutions into CaCl$_2$-treated E. coli JM102 cells using standard techniques and plated in 2×YT top agar on 2×YT agar plates. (2×YT=tryptone 16 g/l, yeast extract 10 g/l, NaCl 5 g/l. 2×YT topagar=2×YT with 0.4% agarose added and autoclaved. 2×YT agar plates=2×YT with 2% agar added and autoclaved). The plates were incubated at 37° C. overnight.

Identification of positive clones

The method used was plaque-lift hybridization as follows: a nitrocellulose filter was placed on a plate with a suitable plaque-density, so that the filter was wetted. The filter was then bathed in the following solutions: 1.5M NaCl, 0.5M NaOH for 30 sec., 1.5M NaCl, 0.5M Tris-HCl, pH 8.0 for 1 min. and 2×SSC (0.3M NaCl, 0.03M sodium citrate) until later use. The filter was dried on 3 MM filter paper and baked for 2 hours at 80° C. in a vacuum oven.

The mutagenisation primer with the sequence 5'-TTTCTTTCAACAAGAAGTTAAGA-3' (SEQ ID NO:3) was labelled radioactively at the 5'-end in a 30 μl volume containing 70 mM Tris-HCl, pH 7.5, 10 mM MgCl$_2$, 5 mM DTT, 10 pmol oligonucleotide, 20 pmol γ-32P-ATP and 3.5 units of T4 polynucleotide kinase. The mixture was incubated at 37° C. for 30 min. and then for 5 min. at 100° C.

The dried filter was prehybridized for 2 hours at 65° C. in 6×SSC, 0.2% bovine serum albumin, 0.2% Ficoll, 0.2% polyvinylpyrrolidone, 0.2% sodium-dodecyl-sulphate (SDS) and 50 μg/ml sonicated salmon sperm DNA. Then, the reaction mixture containing the labelled probe was added to 15 ml of fresh pre-hybridization mix, and the filter was bathed therein overnight at 27° C. with gentle shaking. After hybridization, the filter was washed 3 times each 15 min. in 2×SSC, 0.1% SDS and autoradiographed. After wash in the same solution, but now at 50° C., and another autoradiography, plaques containing DNA-sequences complementary to the mutagenisation primer were identified.

Because the identified clone is a result of a heteroduplex, the plaque was plated again. The hybridization and identification steps were repeated.

Purification of double-stranded M13-phage DNA

A re-screened clone was used for infection of E. coli strain JM101. A culture containing approximately 10$^8$ phages and 5 colonies of JM101 was grown for 5 hours in 5 ml 2×YT medium at 37° C. Then, double-stranded, circular DNA was purified from the pellet according to a method described by Birnboim et al., Nucleic Acids Res. 2, p. 1513 (1979).

Isolation of a restriction fragment encoding modified lipase

The DNA preparation (appr. 5 μg) isolated above was digested with 10 units of each of the restriction endonucleases BamHI and XbaI in 60 μl of 100 mM NaCl, 50 mM Tris-HCl, pH 7.5, 10 mM MgCl$_2$ and 10 mM DTT for 2 hours at 37° C. The DNA products were separated on an agarose gel and the fragment was purified from the gel.

Figure 5:
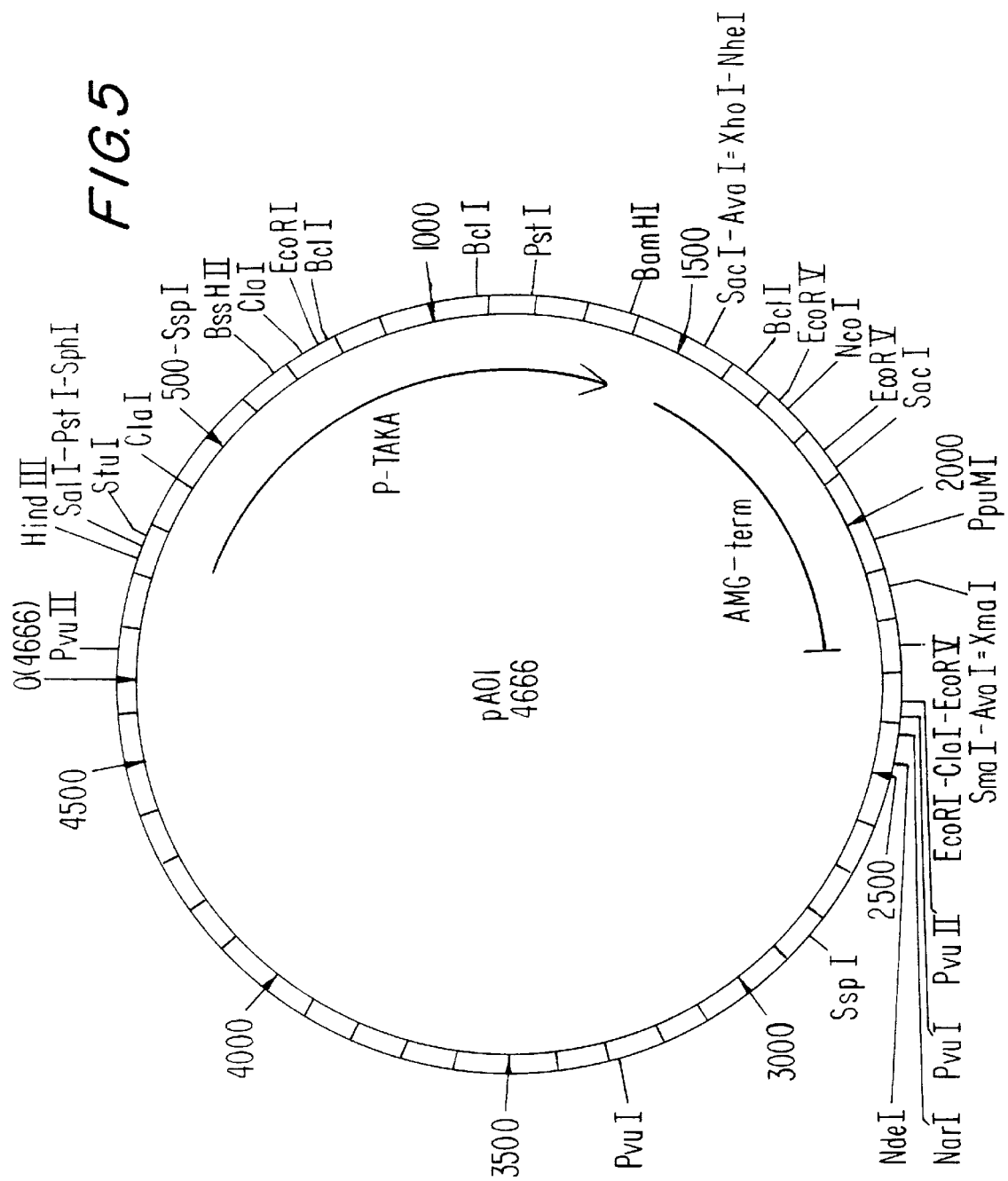
FIG. 5 shows a restriction map of plasmid pAO1.

Ligation to the Aspergillus expression vector pAO1 (FIG. 5)

The isolated restriction fragment was ligated to the Aspergillus vector pAO1 digested with the restriction enzymes BamHI and NheI in the following reaction mixture: Fragment 0.2 μg, vector 0.02 μg, 50 mM Tris-HCl, pH 7.4, 10 mM MgCl$_2$, 10 mM DTT, 1 mM ATP in a total volume of 20 μl. 5 μl of this reaction mix was used for transformation of E. coli strain MC1061, in which the modified expression plasmid was identified and propagated. The plasmid was called pAHLD96L and is identical to pAHL except for the modified codon.

Sequence verification of pAHLD96L

The mutagenized plasmid was sequenced directly on the double-stranded plasmid using the dideoxy chain termination method originally described by Sanger.

Example 2

Construction of Plasmids Expressing other Variants of Humicola Lipase

Other mutant lipase genes were constructed using the same method as described in Example 1. Plasmid names and primers used for the modifications are listed below.

| Plasmid name | Primer sequence |
|---|---|
| pAHLD96N | 5'-TCTTTCAAGTTGAAGTTAAGA-3' (SED ID NO:26) |
| pAHLD111N | 5'-GTGAAGCCGTTATGTCCCCTG-3' (SED ID NO:27) |
| pAHLE87Q | 5'-CGATCCAGTTTTGTATGGAACGA-3' (SED ID NO:28) |
| pAHLR209A/E210A | 5'-GCTGTAACCGAAAGCAGCCGGCGGGAGTCT-3' (SED ID NO:29) |
| pAHLE87A | 5'-CGATCCAGTTAGCTATGGAACG-3' (SED ID NO:30) |
| pAHLE56A | 5'-CTCCAGAGTCAGCAAACGAGTA-3' (SED ID NO:31) |
| pAHLE56Q | 5'-CCAGAGTCTTGAAACGAGTAG-3' (SED ID NO:32) |
| pAHLD111L | 5'-AAGTGAAGCCCAAATGTCCCCTG-3' (SED ID NO:33) |
| pAHLE210A | 5'-TGTAACCGAAAGCGCGGCGG-3' (SED ID NO:34) |
| pAHLE210Q | 5'-TAACCGAATTGGCGCGGCGGG-3' (SED ID NO:35) |
| pAHLR209A | 5'-AACCGAATTCAGCCGGCGGGAGT-3' (SED ID NO:36) |

Example 3

Construction of a Plasmid Expressing the D254N Variant of *Humicola lanuginosa* Lipase Linearization of plasmid pAHL The circular plasmid pAHL was linearized with the restriction enzyme SphI in the following 50 µl reaction mixture: 50 mM NaCl, 10 mM Tris-HCl, pH 7.9, 10 mM $MgCl_2$, 1 mM dithiothreitol, 1 µg plasmid and 2 units of SphI. The digestion was carried out for 2 hours at 37° C. The reaction mixture was extracted with phenol (equilibrated with Tris-HCl, pH 7.5) and precipitated by adding 2 volumes of ice-cold 96% ethanol. After centrifugation and drying of the pellet, the linearized DNA was dissolved in 50 µl $H_2O$ and the concentration estimated on an agarose gel.

3-step PCR mutagenesis

Figure 4:
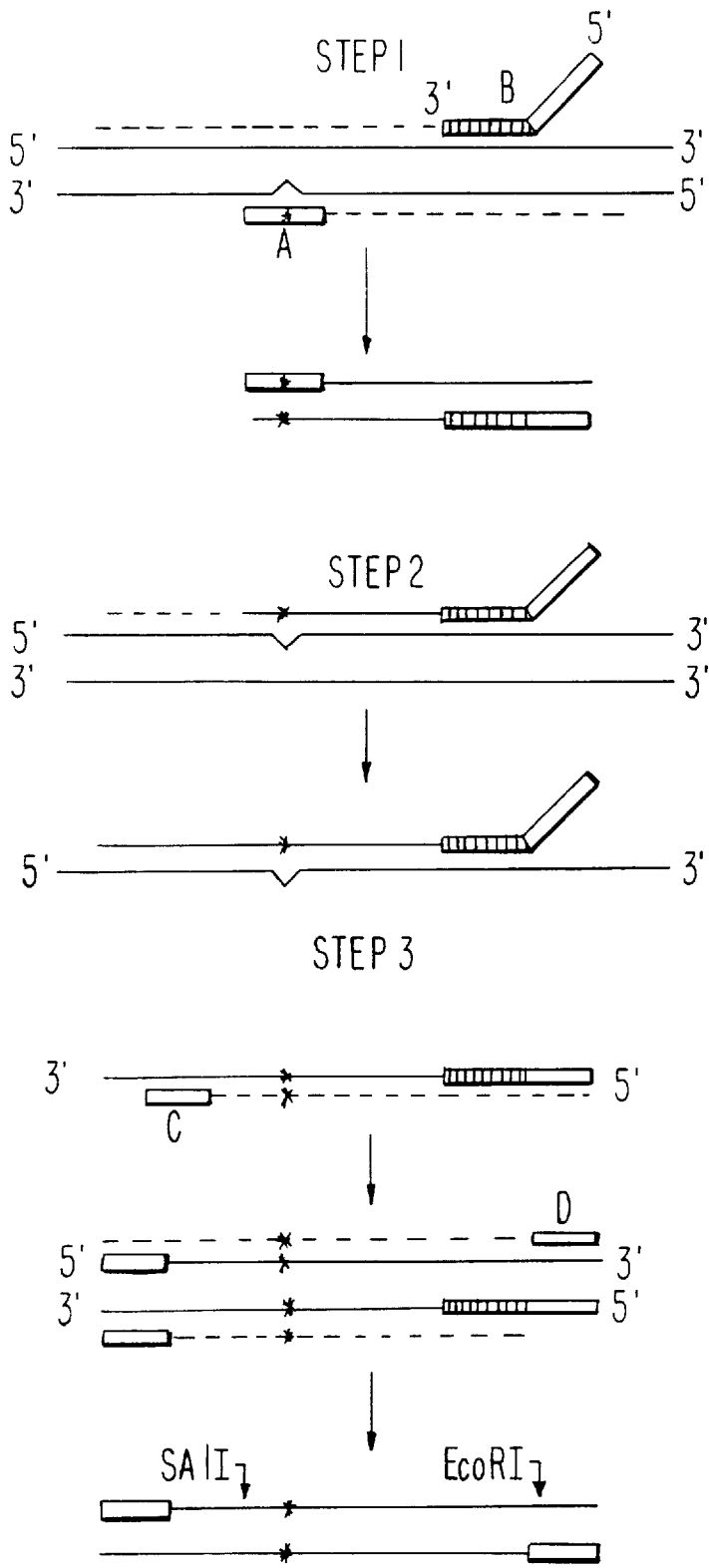
FIG. 4 is a schematic representation of the three-step mutagenesis by PCR.

As shown in FIG. 4, 3-step mutagenisation involves the use of four primers: Mutagenisation primer (=A): 5'-GTGCGCAGGGATGTTCGGAATGTTAGG-3' (SEQ ID NO:37)

PCR Helper 1 (=B): 5'-GGTCATCCAGTCAC-TGAGACCCTCTACCTATTAAATCGGC-3' (SEQ ID NO:11)

PCR Helper 2 (=C): 5'-CCATGGCTTTCACGGTGTCT-3' (SEQ ID NO:12)

PCR Handle (=D): 5'-GGTCATCCAGTCACTGAGAC-3' (SEQ ID NO:13)

Helper 1 and helper 2 are complementary to sequences outside the coding region, and can thus be used in combination with any mutagenisation primer in the construction of a variant sequence.

All 3 steps were carried out in the following buffer containing: 10 mM Tris-HCl, pH 8.3, 50 mM KCl, 1.5 mM $MgCl_2$, 0.001% gelatin, 0.2 mM dATP, 0.2 mM dCTP, 0.2 mM dGTP, 0.2 mM TTP, 2.5 units Taq polymerase.

In step 1, 100 pmol primer A, 100 pmol primer B and 1 fmol linearized plasmid was added to a total of 100 µl reaction mixture and 15 cycles consisting of 2 minutes at 95° C., 2 minutes at 37° C. and 3 minutes at 72° C. were carried out.

The concentration of the PCR product was estimated on an agarose gel. Then, step 2 was carried out. 0.6 pmol step 1 product and 1 fmol linearized plasmid was contained in a total of 100 µl of the previously mentioned buffer and 1 cycle consisting of 5 minutes at 95° C., 2 minutes at 37° C. and 10 minutes at 72° C. was carried out.

To the step 2 reaction mixture, 100 pmol primer C and 100 pmol primer D was added (1 µl of each) and 20 cycles consisting of 2 minutes at 95° C., 2 minutes at 37° C. and 3 minutes at 72° C. were carried out. This manipulation comprised step 3 in the mutagenisation procedure.

Isolation of mutated restriction fragment

The product from step 3 was isolated from an agarose gel and re-dissolved in 20 µl $H_2O$. Then, it was digested with the restriction enzyme BspMII in a total volume of 50 µl with the following composition: 100 mM NaCl, 50 mM Tris-HCl, pH 7.9, 10 mM $MgCl_2$, 1 mM DTF and 10 units of BspMII. Incubation was at 37° C. for 2 hours. The 264 bp BspMIII fragment was isolated from an agarose gel.

Ligation to expression vector pAHL

The expression plasmid pAHL was cleaved with BspMII under conditions indicated above and the large fragment was isolated from an agarose gel. To this vector, the mutated fragment isolated above was ligated and the ligation mix was used to transform *E. coli*. The presence and orientation of the fragment was verified by cleavage of a plasmid preparation from a transformant with restriction enzymes. Sequence analysis was carried out on the double-stranded plasmid using the di-deoxy chain termination procedure developed by Sanger. The plasmid was named pAHLD254N and is identical to pAHL, except for the altered codon.

Example 4

Construction of Plasmids Expressing other Variants of Humicola Lipase

The following mutants were constructed using the same method as described in Example 3, except other restriction enzymes were used for digesting the PCR-product and the vector used for recloning of the mutated fragment. Plasmid names and primers used for the modifications are listed below.

| Plasmid name | Primer A sequence |
|---|---|
| pAHLD254K | 5'-GTGCGCAGGGATCTTCGGAATGTT-3' (SEQ ID NO:4) |
| pAHLD254R | 5'-GTGCGCAGGGATTCTCGGAATGTT-3' (SEQ ID NO:5) |
| pAHLD242N | 5'-GCCGCCGGTGGCGTTGATGCCTTCTAT-3' (SEQ ID NO:6) |
| pAHLD242N/D254N | 5'-GTGCGCAGGGATGTTCGGAATGTTAGGCTGGTTATTGCCGCCGGTGGCGTTGATGCCTTCTAT-3' (SEQ ID NO:7) |

| Plasmid name | Primer A sequence |
|---|---|
| pAHLE87R | 5'-CCCGATCCAGTTTCTTATCGATCGAGAGCCGCGG-3' (SEQ ID NO:8) |
| pAHLE87K | 5'-CGATCCAGTTCTTTATCGATGGAGAGCCACGG-3' (SEQ ID NO:9) |

Example 5

Construction of Lipase Variants by Combination of Available Mutants

The following mutants were constructed by combining plasmid fragments of mutants constructed above. For example, pAHLE87K/D254K was constructed by isolating the BamHI/BstXI restriction fragment from pAHLE87K and inserting the fragment into pAHLD254K digested with BamHI and BstXI:

Plasmid
pAHLE87K/D254K
pAHLE87Q/D254N/D242N/E210Q
pAHLE87Q/D242N/E210Q
pAHLR209A/E210A/D96L
pAHLR209A/E210Q/E56Q
pAHLE210Q/D242N/D254N
pAHLE87Q/E210Q/D242N

Example 6

Construction of a Plasmid Expressing the ΔL264→L269 Variant of *Humicola lanuginosa* Lipase The following mutants were constructed using the same method as described in Example 3, except that the restriction enzymes BglII and BstXI were used for digesting the PCR-product and the vector used for recloning of the mutated fragments. Plasmid names and primers used for the modifications are listed below.

| | |
|---|---|
| Mutagenisation primer (= A): | 5'-CAGGCGCGCCGGCCACCCGAAGTACCATAG-3' (SEQ ID NO:10) |
| PCR Helper 1 (= B): | 5'-GGTCATCCAGTCACTGAGACCCTCTACCTATTAAATCGGC-3' (SEQ ID NO:11) |
| PCR Helper 2 (= C): | 5'-CCATGGCTTTCACGGTGTCT-3' (SEQ ID NO:12) |
| PCR Handle (= D): | 5'-GGTCATCCAGTCACTGAGAC-3 (SEQ ID NO:13) |

Example 7

Construction of Plasmids Expressing other Variants of Humicola Lipase

The following mutants were constructed using the same method as described in Example 6, except that other restriction enzymes were used for digesting the PCR-product and the vector used for recloning of the mutated fragment. Plasmid names and primers used for the modifications are listed below.

| Plasmid name | Primer A sequence |
|---|---|
| pAHLΔN247 -> D254 | 5'-TAGGTGCGCAGGGATCGGAATGTTAGGCTGGTTGCCGCCGGTGGCATC-3' (SEQ ID NO:14) |
| pAHLE239* + I241* + D242* | 5'-ATTGCCGCCGGTGGCGCCTATCTTCACGATATC-3' (SEQ ID NO:15) |

Example 8

Construction of the Lipase Variant L206V by Cassette Mutagenesis

Using the method outlined in Example 6, the coding sequence on plasmid pAHL was modified to contain unique AvrII and MluI sites. The AvrII site was made by changing the G681 of the coding sequence to an adenosine. The MluI site was made by changing C759 to G and A762 to T. The new plasmid was named pAHL7 and encodes the same lipase as pAHL. Between the AvrII- and MluI-sites the following synthetically made linker was inserted (changes the Leu-codon to a Val-codon and deletes the ScaI-site for easy screening among transformants) (SEQ ID NO:16):

```
                 ***
AvrII       CTAGGGTTCCGCCGCGCGAATTCGGTTACAGCCATTCT
                CCAAGGCGGCGCGCTTAAGCCAATGTCGGTAAGA
            ArgValProProArgGluPheGlyTyrSerHisSer -
            205            210            216
                 *
     AGCCCAGAATACTGGATCAAATCTGGAACCCTTGTCCCCGTCA    MluI
     TCGGGTCTTATGACCTAGTTTAGACCTTGGGAACAGGGGCAGTGCGC
     SerProGluTyrTrpIleLysSerGlyThrLeuValProValThrArg
     217     220         225         230
```

The resulting plasmid was named pAHLL206V, and is identical to pAHL, except for the changed bases.

Example 9

Construction of other Lipase Variants Using Cassette Mutagenesis

Other mutants constructed by cassette mutagenesis as described in Example 8 are listed below. Other linkers were used for introducing the appropriate mutations.
Plasmid name
pAHLL206A
pAHLF211V
pAHLF211A
pAHLDR209/E210

Example 10

Construction of a Plasmid Expressing the D62C+E87C Variant of *Humicola lanuginosa* Lipase The following mutants were constructed using the same method as described in Example 3, except that the restriction enzymes BamHI and BstXI were used for digesting the PCR-product and the vector used for recloning of the mutated fragments. Plasmid names used for the modification are listed below.

| | |
|---|---|
| Mutagenisation primer (= A) | 5'-ATTCCCGATCCAGTTACATATGGAACGAGAGCCACGGAAGCTTAGGACGATCAATTTGTT CGTGTTGTCGAGAGCAAGGAAGCCGGTGACACAGCCCACTCCAGAGTC-3' (SEQ ID NO:18) |
| PCR Helper 1 (= B): | 5'-GGTCATCCAGTCACTGAGACCCTCTACCTATTAAA—TCGGC-3' (SEQ ID NO:19) |
| PCR Helper 2 (= C): | 5'-CCATGGCTTTCACGGTGTCT-3' (SEQ ID NO:20) |
| PCR Handle (= D): | 5'-GGTCATCCAGTCACTGAGAC-3' (SEQ ID NO:21) |

Example 11

Construction of Plasmids Expressing other Variants of Humicola Lipase

The following mutants were constructed using the same method as described in Example 10, except that other restriction enzymes were used for digesting the PCR-product and the vector used for recloning of the mutated fragment. Plasmid names and primers used for the modifications are listed below.

| Plasmid name | Primer A sequence |
|---|---|
| pAHLG61C/E87C | 5'-AAGATTCCCGATCCAACACTCTATGGAACGAGAGCCACGGAAG-CTTAGGACGATCAATTTGTTCGTGTTGTCGAGAGCAAGGAAGCCGG-TGACATCACACACTCCAGAGTCTTC-3' (SEQ ID NO:22) |
| pAHLI255T/L259T | 5'-TAACCCGAAGTACCAAGTGTGCGCAGGAGTATCCGGAATGTTAG-3' (SEQ ID NO:23) |

Example 12

Construction of the Lipase Variant L206V by Cassette Mutagenesis

Using the method outlined in Example 3, the coding sequence on plasmid pAHL was modified to contain unique AvrII and MluI sites. The AvrII site was made by changing the G681 of the coding sequence to an adenosine. The MluI site was made by changing C759 to G and A762 to T. The new plasmid was named pAHL7 and encodes the same lipase as pAHL. Between the AvrII- and MluI-sites the following synthetically made linker was inserted (changes the Leu-codon to a Val-codon and deletes the ScaI-site for easy screening among clones with the linker cloned) (SEQ ID NO:24):

```
      ***
CTAGGGTTCCGCCGCGCGAATTCGGTTACAGCCATTCT
      CCAAGGCGGCGCGCTTAAGCCAATGTCGGTAAGA
   ArgValProProArgGluPheGlyTyrSerHisSer -
   205           210           216
               *
AGCCCAGAATACTGGATCAAATCTGGAACCCTTGTCCCCGTCA
TCGGGTCTTATGACCTAGTTTAGACCTTGGGAACAGGGGCAGTGCGC
SerProGluTyrTrpIleLysSerGlyThrLeuValProValThrArg
217      220           225           230
```

The resulting plasmid was named pAHLL206V, and is identical to pAHL, except for the changed bases.

enzymes BamHI and BstXI were used for digesting the PCR-product and the vector used for recloning of the mutated fragments. Primers used for the modifications are listed below.

| | |
|---|---|
| Mutagenisation primer (= A): | 5'-ATTTATTTCTTTCAACCAGAAGTTAAGATTCCC-3' (SEQ ID NO:38) |
| PCR Helper 1 (= B): | 5'-GGTCATCCAGTCACTGAGACCCTCTACCTATTAAATCGGC3' (SEQ ID NO:11) |
| PCR Helper 2 (= C): | 5'-CCATGCCTTTCACGGTGTCT-3' (SEQ ID NO:12) |
| PCR Handle (= D): | 5'-GGTCATCCAGTCACTGAGAC-3' (SEQ ID NO:13). |

Example 13
Construction of other Lipase Variants Using Cassette Mutagenesis Other mutants constructed by cassette mutagenesis as described in Example 3 are listed below. Other linkers were used for introducing the appropriate mutations.

Plasmid name
pAHLL206T
pAHLL206S
pAHLL206A
pAHLL206G
pAHLF211L
pAHLF211T
pAHLF211K

Example 14
Construction of Lipase Variants by Combination of Available Mutants The following mutants were constructed by combining plasmid fragments of mutants constructed above. For example, pAHLG61C+E87C was constructed by isolating the HindIII restriction fragment from pAHLD62C+E87C (the primer used for the construction introduced a HindIII site between the two mutations) and inserting the fragment into pAHLG61C+N88C digested with HindIII (also introduced together with the mutations):
Plasmid
pAHLD61C+E87C
pAHLL206S+I255T+L259T

Example 15
Construction of a Plasmid Expressing the D96W Variant of H. lanuginosa Lipase The following mutants were constructed using the same method as described in Example 3, except that the restriction

Example 16

Construction of Plasmids Expressing other Variants of H. lanuginosa Lipase

The following mutants were constructed using the same method as described in Example 15, except that the restriction enzymes XhoI and BstXI were used for digesting the PCR-product and the vector used for recloning of the mutated fragments for D254K/L259I and L259I. Plasmid names and primers used for the modifications are listed below.

| Plasmid name | Primer A sequence |
|---|---|
| pAHLD96F | 5'-ATTTATTTCTTTCAAGAAGAAGTTAAGATTCCC-3' (SEQ ID NO:39) |
| pAHLD96V | 5'-ATTTATTTCTTTCAAAACGAAGTTAAGATTCCC -3' (SEQ ID NO:40) |
| pAHLL259I | 5'-CCGAAGTACCAAATGTGAGCAGGGATATCC-3' (SEQ ID NO:41) |
| pAHLD25K + L259I | 5'-CCGAAGTACCAAATGTGAGCAGGGATCTTCGGAATGTTAGG-3' (SEQ ID NO:42) |

Example 17
Construction of Random Lipase Variants

Random mutagenized libraries of the entire H. lanuginosa lipase gene and of amino acids (aa) 91–97 and 206–211 thereof were prepared as described in Materials and Methods above.

The amino acid regions 91–97 and 206–211 were chosen for the first round of localized mutagenesis since these regions have been found to be important for wash performance. Region 91–97 is a part of the lid region of the lipase and region 206–211 constitutes part of the hydrophobic cleft of the lipase.

One oligonucleotide was synthesized for each of these regions comprising 93% of the wild type nucleotides and 2.33% of each of the other three nucleotides at amino acid codons wanted to be mutagenized. Where possible without changing the amino acid, the third nucleotide (the wobble base) in codons were synthesized with 50% G/50% C to give a larger likelyhood for changes to amino acids with one or two codons. The composition of the mutagenic oligonucleotide of region 91–97 is shown in Table 1.

By use of this oligonucleotide a calculated mutation frequency of approximately 65–70% is obtained in the library for one amino acid change having been introduced in the parent lipase. The mutation frequency for two or more amino acid changes having been introduced are less than 35%. This low mutation frequency is chosen to ensure that the observed amino acid changes in positive clones are involved in improving the enzyme and not just "neutral" changes due to a high mutation frequency.

The mutagenic primer were used in a PCR reaction with a suitable opposite primer. The resulting PCR fragment were purified and in the case of region 206–211 digested and cloned into the shuttle vector. In the case of region 91–97 the resulting PCR fragment was used in a second PCR reaction as a primer with a second suitable opposite primer. This step was necessary to be able to digest and clone the mutagenized region into the shuttle vector.

Libraries of region 91–97 and of region 206–211 have been prepared containing from 10,000 to 80,000 clones/library. Most colonies were positive (more than 90%) when checked under conditions where the parent lipase is positive, i.e., exhibits lipase activity. The positive reaction was determined in a filter assay with 2.5 mM Ca (instead of 5 mM EGTA).

450,000 colonies were screened from the different libraries using the Dobanol™ 25-7 and low calcium assays described in Materials and Methods above. 25 low calcium positives from the aa 91–97 library (lid-region) and twelve Dobanol™ 25-7 positives from the whole gene libraries were isolated. Fourteen of the low calcium positives from mutagenesis of aa 91–97 were sequenced.

The three other mutations (in codon 83, 103, 145), outside the mutagenized region, can be explained by PCR misincoorperation, allthough the mutation of S83T is a transversion which is quite unusual for PCR misincoorperations.

TABLE 1

Illustration of the construction of oligonucleotides used for localized random mutagensis of amino acids 91–97 of Lipolase ®. The numbers presented in the sequence refer to the bottles the composition of which is appearing to the right of the sequence.

Sequence:

| 5' | 5 | C | G |  |
|---|---|---|---|---|
| T | 5 | C | 3' |  |
| T | 7 | A |  |  |
| A | 8 | G |  | Bottle 5: 93% A; 2.33% C; 2.33% G and 2.33% T |
| T | 8 | T |  |  |
| T | A/C | T |  |  |
| T | 5 | C |  |  |
| C | 7 | T |  |  |
| T | 5 | C |  | Bottle 6: 93% C; 2.33% A; 2.33% G and 2.33% T |
| T | 8 | T |  |  |
| T | 8 | A |  |  |
| 6 | C/G | T |  |  |
| 5 | 6 | G |  | Bottle 7: 93% G; 2.33% A; 2.33% C and 2.33% T |
| 5 | 6 | G |  |  |
| 7 | G | A |  |  |
| 8 | A | A |  |  |
| 6 | T | C |  | Bottle 8: 93% T; 2.33% A; 2.33% C and 2.33% G |
| 7 |  |  |  |  |

TABLE 2

Strain number refers to the originally picked clones cloned into Aspergillus expression vector pAHL. Variant type refers to identical clones, which probably have arisen during amplification of the random mutagenized library. Variant types I and II are active in 0.01% Dobano ™ 25-7 while the rest are inactive like wild type.

| Strain number | Variant type | | | | | |
|---|---|---|---|---|---|---|
| 59 | I |  |  | G91A | N94K | D96A |
| 60 | II | S83T |  |  | N94K | D96N |
| 61 | II | S83T |  |  | N94K | D96N |
| 62 | III |  | E87K |  |  | D96V |
| 63 | IV |  | E87K | G91A |  | D96V |
| 64 | II | S83T |  |  | N94K | D96N |
| 65 | III |  | E87K |  |  | D96V |
| 67 | V |  |  |  | N94K F95L | D96H |
| 69 | V |  |  |  | N94K F95L | D96H |
| 71 | III |  | E87K |  |  | D96V |
| 72 | II | S83T |  |  | N94K | D96N |

TABLE 3

The wildtype sequence is shown at the topline. Only nucleotides differing from wt are written at the variant sequences. The base of codon 91 and 93 were doped with 1:1 of C/T and T/G, respectively. Otherwise the nucleotides at codon 91–97 were doped using 93% wt and 2.33% of the three other nucleotides.

| Strain number | Variant type | DNA sequence (Amino acid number above the sequence) | | | | | | | | | |
|---|---|---|---|---|---|---|---|---|---|---|---|
|  |  | 82 | 83 | 84 | 85 | 86 | 87 | 88 | 89 | 90 | 91 | 92 |
| wt |  | GGC | TCT | CGT | TCC | ATA | GAG | AAC | TGG | ATC | GGG | AAT |
| 59 | I |  |  |  |  |  |  |  |  |  | C |  |
| 60 | II |  | A |  |  |  |  |  |  |  | C |  |
| 61 | II |  | A |  |  |  |  |  |  |  | C |  |
| 62 | III |  |  |  |  |  | A |  |  |  | C |  |
| 63 | IV |  |  |  |  |  | A |  |  |  | C |  |
| 64 | II |  | A |  |  |  |  |  |  |  | C |  |
| 65 | III |  |  |  |  |  | A |  |  |  | C |  |
| 67 | V |  |  |  |  |  |  |  |  |  | C |  |
| 52/68 | wt |  |  |  |  |  |  |  |  |  |  |  |
| 53 | wt |  |  |  |  |  |  |  |  |  |  |  |
| 69 | V |  |  |  |  |  |  |  |  |  | C |  |
| 71 | III |  |  |  |  |  | A |  |  |  | C |  |

TABLE 3-continued

The wildtype sequence is shown at the topline. Only nucleotides differing from wt are written at the variant sequences. The base of codon 91 and 93 were doped with 1:1 of C/T and T/G, respectively. Otherwise the nucleotides at codon 91–97 were doped using 93% wt and 2.33% of the three other nucleotides.

| Strain number | Variant type | DNA sequence (Amino acid number above the sequence) | | | | | | | | | |
|---|---|---|---|---|---|---|---|---|---|---|---|
| 72 | II | A | | | | | | | | C | |
| 73 | VI | | | | | | | | | | |
| | | 93 | 94 | 95 | 96 | 97 | 98 | 99 | 100 | -103 | -145 |
| wt | | CTT | AAC | TTC | GAC | TTG | AAA | GAA | ATA | -ATT | -CAT |
| 59 | I | G | G | | C | | | | | | |
| 60 | II | G | G | | A | | | | | | |
| 61 | II | G | G | | A | | | | | | |
| 62 | III | | | | T | | | | | | |
| 63 | IV | | | | C | | | | | C | C |
| 64 | II | G | G | | A | | | | | | |
| 65 | III | G | | | T | | | | | | |
| 67 | V | | A | C A C | | | | | | | |
| 52/68 | wt | | | | | | | | | | |
| 53 | wt | | | | | | | | | | |
| 69 | V | | A | C A C | | | | | | | |
| 71 | III | G | | | T | | | | | | |
| 72 | II | G | A | | A | | | | | | |
| 73 | VI | | | | A | ? | | | | | |

Example 18

Analogously to the method described in Example 17, the following variants were constructed by random mutagenesis. The actual screening criteria used for selecting some of the variants are also described.
D167G+E210V
5 mM EGTA,0.01% Dobanol™ 25-7,0.006% LAS
E87K+G91A+L93I+N94K+D96A
5 mM EGTA,0.02% Dobanol™ 25-7
N73D+S85T+E87K+G91A+N94K+D96A
S83T+E87K+W89G+G91A+N94K+D96V
E87K+G91A+D96R+I100V
S83T+E87K+Q249R
E87K+G91A Example 19

Construction of a Plasmid Expressing the N94K/D96A Analogue of *Humicola lanuginosa* Lipase The following variant was constructed using the same method used in Example 15. The primers used for the modification are listed below.

Mutagenisation primer (=A):
5'-TATTTCTTTCAAAGCGAACTTAAGATTCCCGAT-3' (SEQ ID NO:43)
PCR Helper 1 (=B): 5'-GGTCATCCAGTCACTGAGA-CCCTCTACCTATTAAATCGGC-3' (SEQ ID NO:11)
PCR Helper 2 (=C): 5'-CCATGGCTTTCACGGTGTCT-3' (SEQ ID NO:12)
PCR Handle (=D): 5' -GGTCATCCAGTCACTGAGAC-3' (SEQ ID NO:13)

Example 20

Construction of Plasmids Expressing other Variants of Humicola Lipase

The following variants were constructed using the same method as in Example 15. Plasmid names and primers used for these modifications are listed below.

| Plasmid name | Primer A sequence |
|---|---|
| pAHLS83T/N94K/D96A | 5'-ATTTCTTTCAAAGCGAACTTAAGATTCCCGATCCAGTTCTCTATG GAACGAGTGCCACGGAAAGA-3' (SEQ ID NO 44) |
| pAHLE87K/D96V | 5-TATTTCTTTCAAAACGAAGTTAAGATTCCCGATCCAGTTCTTTAT-GGAACGAGA-3' (SEQ ID NO 45) |
| pAHLE87K/G91A/D96A | 5'-TATTTCTTTCAAAAGCGAAGTTAAGATTAGCGATCCAGTTCTTTAT-GGAACGAGA-3' (SEQ ID NO 46) |
| pAHLN94K/F95L/D96H | 5'-TATTTCTTTCAAGTGCAACTTAAGATTCCCGAT-3' (SEQ ID NO 47) |
| pAHLF95C/D96N | 5'-TATTTCTTTCAAGTTACAGTTAAGATTCCC-3' (SEQ ID NO 48) |
| pAHLG91S/L93V/F95C | 5'-TATTTCTTTCAAGTCACAGTTAACATTAGAGATCCAGTTCTC-3' (SEQ ID NO 49) |
| pAHLE87K/G91A/L93I/N94K/D96A | 5'-TATTTCTTTCAAAAGCGAACTTAATATTAGCGATCCAGTTCTTTAT-GGAACGAGA-3' (SEQ ID NO 50) |
| pAHLD167G | 5'-ATATGAAAACACACCGATATCATACCC-3' (SEQ ID NO 51) |
| pAHLA121V | 5'-CCTTAACGTATCAACTACAGACCTCCA-3' (SEQ ID NO 52) |
| pAHLR205K/E210Q | 5'-GCTGTAACCGAATTGGCGCGGCGGGAGCTTAGGGACAATATC-3' (SEQ ID NO 53) |
| pAHLN73D/S85T/E87K/G91A/N94K/D96A | 5'-TATTTCTTTCAAAGCGAACTTAAGATTAGCGATCCAGTTCTTTATAG-TACGAGAGCCACGGAAAGAGAGGACGATCAATTTGTCCGTGTTGTCGAG-3' (SEQ ID NO 54) |

| Plasmid name | Primer A sequence |
|---|---|
| pAHLS83T/E87K/W89G/G91A/N94K/D96V | 5'-TATTTCTTTCAAAACGAACTTAAGATTAGCGATACCGTTCTTTAT-GGAACGAGTGCCACGGAAAGA-3' (SEQ ID NO 55) |
| pAHLE87K/G91A/D96R/I100V | 5'-GCAAATGTCATTAACTTCTTTCAATCTGAAGTTAAGATTAGCGAT-CCAGTTCTTTATGGAACGAG-3' (SEQ ID NO 56) |
| pAHLS83T/E87K | 5'-CCCGATCCAGTTCTTTATGGAACGAGTGCCACGGAAAGA-3' (SEQ ID NO 57) |
| pAHLE87K/G91A | 5'-GAGGTTAAGATTAGCGATCCAGTTCTTTATGGAACGAGA-3' (SEQ ID NO 58) |
| pAHLS83T/E87K | 5'- CCCGATCCAGTTCTTTATGGAACGAGTGCCACGGAAAGA-3' (SEQ ID NO 59) |
| pAHLQ249R | 5' CGGAATGTTAGGTCTGTTATTGCCGCC-3' (SEQ ID NO 60) |

Example 21

Construction of Plasmids Expressing Combination Analogues of Humicola Lipase

The plasmids pAHLD167G/E210V, pAHLA121V/R205K/E210Q and pAHLS83T/E87K/Q249R were constructed by performing two successive mutagenisation steps using the appropriate primers.

Example 22

Expression of Lipase Variants in Aspergillus

Transformation of *Aspergillus oryzae* (general procedure)

100 ml of YPD (Sherman et al., Methods in Yeast Genetics, Cold Spring Harbor Laboratory (1981)) was inoculated with spores of *A. oryzae* and incubated with shaking for about 24 hours. The mycelium was harvested by filtration through miracloth and washed with 200 ml of 0.6M MgSO$_4$. The mycelium was suspended in 15 ml of 1.2M MgSO$_4$, 10 mM NaH$_2$PO$_4$, pH=5.8. The suspension was cooled on ice and 1 ml of buffer containing 120 mg of Novozym® 234, batch 1687 was added. After 5 min., 1 ml of 12 mg/ml BSA (Sigma type H25) was added and incubation with gentle agitation continued for 1.5–2.5 hours at 37° C. until a large number of protoplasts was visible in a sample inspected under the microscope.

The suspension was filtered through miracloth, the filtrate transferred to a sterile tube and overlayed with 5 ml of 0.6M sorbitol, 100 mM Tris-HCl, pH=7.0. Centrifugation was performed for 15 min. at 1000 g and the protoplasts were collected from the top of the MgSO$_4$ cushion. 2 volumes of STC (1.2M sorbitol, 10 mM Tris-HCl, pH=7.5, 10 mM CaCl$_2$) were added to the protoplast suspension and the mixture was centrifugated for 5 min. at 1000 g. The protoplast pellet was resuspended in 3 ml of STC and repelleted. This was repeated. Finally, the protoplasts were resuspended in 0.2–1 ml of STC.

100 µl of protoplast suspension was mixed with 5–25 µg of p3SR2 (an *A. nidulans* amdS gene carrying plasmid described in Hynes et al., *Mol. and Cel. Biol.* 3(8), 1430–39 (1983)) in 10 µl of STC. The mixture was left at room temperature for 25 min. 0.2 ml of 60% PEG 4000 (BDH 29576), 10 mM CaCl$_2$ and 10 mM Tris-HCl, pH=7.5 was added and carefully mixed (twice) and finally 0.85 ml of the same solution was added and carefully mixed. The mixture was left at room temperature for 25 min., spun at 2.500 g for 15 min. and the pellet was resuspended in 2 ml of 1.2M sorbitol. After one more sedimentation the protoplasts were spread on minimal plates (Cove, *Biochem. Biophys. Acta* 113, pp. 51–56 (1966)) containing 1.0M sucrose, pH=7.0, 10 mM acetamide as nitrogen source and 20 mM CsCl to inhibit background growth. After incubation for 4–7 days at 37° C. spores were picked, suspended in sterile water and spread for single colonies. This procedure was repeated and spores of a single colony after the second reisolation were stored as a defined transformant.

Expression of lipase variants in *A. oryzae*

The plasmids described above were transformed into *A. oryzae* IFO 4177 by cotransformation with p3SR2 containing the amdS gene from *A. nidulans* as described above. Protoplasts prepared as described were incubated with a mixture of equal amounts of the expression plasmid and p3SR2, approximately 5 µg of each were used. Transformants which could use acetamide as sole nitrogen source were reisolated twice. After growth on YPD for three days, culture supernatants were analyzed using the assay for lipase activity. The best transformant was selected for further studies and grown in a 1 l shake-flask on 200 ml FG4 medium (3% soy meal, 3% maltodextrin, 1% peptone, pH adjusted to 7.0 with 4M NaOH) for 4 days at 30° C.

Example 23

Purification of Lipase Variants of the Invention

Assay for lipase activity

A substrate for lipase was prepared by emulsifying glycerine tributyrat (MERCK) using gum-arabic as emulsifier.

Lipase activity was assayed at pH 7 using pH stat method. One unit of lipase activity (LU/mg) was defined as the amount needed to liberate one micromole fatty acid per minute.

Step 1: Centrifuge the fermentation supernatant, discard the precipitate. Adjust the pH of the supernatant to 7 and add gradually an equal volume of cold 96% ethanol. Allow the mixture to stand for 30 minutes in an ice bath. Centrifuge and discard the precipitate.

Step 2: Ion exchange chromatography. Filter the supernatant and apply on DEAE-fast flow (Pharmacia ™) column equilibrated with 50 mM tris-acetate buffer pH 7. Wash the column with the same buffer until absorption at 280 nm is lower than 0.05 OD. Elute the bound enzymatic activity with linear salt gradient in the same buffer (0 to 0.5M NaCl) using five column volumes. Pool the fractions containing enzymatic activity.

Step 3: Hydrophobic chromatography. Adjust the molarity of the pool containing enzymatic activity to 0.8M by adding solid Ammonium acetate. Apply the enzyme on TSK gel Butyl-Toyopearl 650 C column (available from Tosoh Corporation Japan) which was pre-equilibrated with 0.8M ammonium acetate. Wash the unbound material with 0.8M ammonium acetate and elute the bound material with distilled water.

Step 4: Pool containing lipase activity is diluted with water to adjust conductance to 2 mS and pH to 7. Apply the pool on High performance Q Sepharose (Pharmacia) column pre-equilibrated with 50 mM tris-acetate buffer pH 7. Elute the bound enzyme with linear salt gradient.

Example 24

Washing Performance of Lipase Variants of the Invention

The washing performance of *Humicola lanuginosa* lipase variants of the invention was evaluated on the basis of the enzyme dosage in mg of protein per liter according to $OD_{280}$ compared to the wild-type *H. lanuginosa* lipase.

Wash trials were carried out in 150 ml beakers placed in a thermostated water bath. The beakers were stirred with triangular magnetic rods.

The experimental conditions were as follows:

| | |
|---|---|
| Method: | 3 cycles with overnight drying between each cycle |
| Wash liquor: | 100 ml per beaker |
| Swatches: | 6 swatches (3.5 × 3.5 cm) per beaker |
| Fabric: | 100% cotton, Test Fabrics style #400 |
| Stain: | Lard colored with Sudan red (0.75 mg dye/g of lard). 6 µl of lard heated to 70° C. was applied to the center of each swatch. After application of the stain, the swatches were heated in an oven at 75° C. for 30 minutes. The swatches were then stored overnight at room temperature prior to the first wash. |
| Detergent: | LAS (Nansa 1169/P, 30% a.m.) 1.17 g/l |
| | AEO (Dobanol 25-7) 0.15 g/l |
| | Sodium triphosphate 1.25 g/l |
| | Sodium sulphate 1.00 g/l |
| | Sodium carbonate 0.45 g/l |
| | Sodium silicate 0.15 g/l |
| | pH: 10.2 |
| Lipase conc.: | 0.075, 0.188, 0.375, 0.75 and 2.5 mg of lipase protein per liter |
| Time: | 20 minutes |
| Temperature: | 30° C. |
| Rinse: | 15 minutes in running tap water |
| Drying: | overnight at room temperature (~20° C., 30–50% RH) |
| Evaluation: | after the 3rd wash, the reflectance at 460 nm was measured. |

Results

Dose-response curves were compared for the lipase variants and the native *H. lanuginosa* lipase. The dose-response curves were calculated by fitting the measured data to the following equation:

$$\Delta R = \Delta R_{max} \, C^{0.5}/(K + C^{0.5}) \quad (I)$$

where $\Delta R$ is the effect expressed in reflectance units, C is the enzyme concentration (mg/l), $\Delta R_{max}$ is a constant expressing the maximum effect, K is a constant; $K^2$ expresses the enzyme concentration at which half of the maximum effect is obtained.

Based on the characteristic constants $\Delta R_{max}$ and K found for each lipase variant as well as the wild-type lipase, improvement factors were calculated. The improvement factor, defined as $$f_{improve} = C_{WT}/C \quad (II)$$

expresses the amount of lipase variant protein needed to obtain the same effect as that obtained with 0.25 mg/l of the reference wild-type protein ($C_{WT}$).

Thus, the procedure for calculating the improvement factor was as follows:

1) The effect of the wild-type protein at 0.25 mg/l ($\Delta R_{wild-type}$) was calculated by means of equation (I);
2) the concentration of lipase variant resulting in the same effect as the wild-type at 0.25 mg/l was calculated by means of the following equation:

$$C = (K_{(variant)}(\Delta R_{(wild-type)}/(\Delta R_{max(variant)} - \Delta R_{(wild-type)})))^2 \quad (III)$$

3) the improvement factor was calculated by means of equation (II).

The results are shown in Tables 4–7 below.

TABLE 4

| Variant | Improvement factor |
|---|---|
| E56A | 1.6 |
| E56Q | 2.6 |
| E56Q + D96L + R209A + E210A | 1.5 |
| E87A | 1.0 |
| D96L | 4.4 |
| D96L + R209A + E210A | 2.8 |
| D111L | 1.0 |
| L206A | 1.0 |
| L206S | 1.3 |
| L206V | 1.6 |
| R209A | 1.1 |
| R209A + E210A | 1.9 |
| R209* + E210* | 0.9 |
| E210Q + D242N + D254N | 1.8 |
| F211A | 0.7 |
| F211I | 1.1 |
| F211L | 1.0 |
| D242N | 1.7 |

Table 4 shows that the lipase variants R209A+E210A, E56Q and D96L have a considerably better wash performance than the wild-type lipase. This might possibly be ascribed to the decreased negative charge and increased hydrophobicity of these variants resulting in increased adsorption during washing and consequently higher activity during the drying phase. The performance of the lipase variants E87A, D111L and R209A is on a par with that of the wild-type enzyme.

TABLE 5

| Variant | Improvement factor |
|---|---|
| D96F | 1.7 |
| D96K | 4.0 |
| D96W | 2.7 |
| D96W + D102N | 3.4 |
| D254K + L259I | 1.7 |
| L259I | 1.2 |

Table 5 shows that the lipase variants D96K, D96W, D96W+E210N and to a certain extent the lipase variants D96F and D254K+L259I have a considerably better wash performance than the wild-type lipase. One possible explanation of this improved effect may be that the charge characteristic of the lipid contact zone of the variants have been changed.

TABLE 6

| Variant | Improvement factor |
|---|---|
| E87K + D96V | 1.2 |
| S83T + N94K + D96N | 2.3 |
| N94K + D96A | 2.7 |
| E87K + G91A + D96A | 2.6 |
| N94K + F95L + D96H | 3.3 |
| D167G + E210V | 5.0 |
| E87K + G91A + L93I + N94K + D96A | 1.3 |
| E87K + G91A + D96R + I100V | 5.2 |
| E87K + G91A | 5.0 |
| N73D + E87K + G91A + N94I + D96G | 1.3 |
| S83T + E87K + G91A + N92H + N94K + D96M | 3.8 |
| K46R + E56R + G61S | 1.9 |
| D102K | 0.2 |
| D167G | 1 |
| N73D + E87K + G91A + N94I + D96G | 1.3 |
| E210R | 2.7 |
| EZ10W | 5.5 |

TABLE 6-continued

| Variant | Improvement factor |
|---|---|
| E210W | 1 |
| N251W + D254W + T267W | 0.8 |
| S83T + E87K + G91A + N92H + N94K + D96M | 3.8 |
| E56R + I90F + D96L + E99K | 4.8 |
| D57G + N94K + D96L + L97M | 1.9 |

TABLE 7

| Variant | Improvement Factor |
|---|---|
| E87K + G91A + D167G + E210V | 7.7 |
| E56R + I90F + D96L + E99K | 4.8 |
| E56R + D57L + V60M + D62N + S83T + D96P + D102E | 1.5 |
| D57G + N94K + D96L + L97M | 1.9 |
| E87K + G91A + E210K | 2.4 |
| N94K + F95L + D96H + Q249R | 0.8 |
| E87K + G91A + Q249R | 12.6 |
| D57G + N94K + D96L + L97M + Q249R | |
| D57G + N94K + D96L + L97M + E210K | |

Example 25

Increased Thermostability of Lipase Variants

The thermostability of selected variants of *H. lanuginosa* lipase was examined by Differential Scanning Calorimetry (DSC). Using this technique, the thermal denaturation temperature, Td, is determined by heating an enzyme solution at a constant programmed rate.

Experiments

The Differential Scanning Calorimeter, MC-2D, from MicroCal Inc. was used for the investigations. 50 mM buffer solutions in was prepared at the following pH-values: 4 (acetate), 7 (TRIS-acetate), 10 (glycine). The enzyme concentration ranged between 0.6–0.9 mg/ml, and a total volume of ca. 1.2 ml was used for each experiment. All samples were heated from 5° C. to 95° C. at a scan rate of 90° C./hr.

Results

The results for the wild type and selected mutants are shown in the table below.

| No | Mutation | pH4 Td | pH4 dTd | pH7 Td | pH7 dTd | pH10 Td | pH10 dTd |
|---|---|---|---|---|---|---|---|
| WT | — | 58.9 | — | 74.7 | — | 69.3 | — |
| 1 | F211A | 60.2 | +1.3 | 75.8 | +1.1 | 70.3 | +1.0 |
| 2 | T267R | 59.4 | +0.5 | 75.7 | +1.0 | 70.0 | +0.7 |
| 3 | D111N | 58.3 | -0.6 | 75.6 | +0.9 | 69.9 | +0.6 |
| 4 | F211L | 57.8 | -1.1 | 74.8 | +0.1 | 69.4 | +0.1 |

Note:
dTd denotes the change in thermostability as a result of the mutation.

Example 26

Storage Stability of *H. lanuginosa* Lipase Variants in Liquid Detergent

Several variants were tested in a model liquid detergent with the following composition:

| | | % w/w |
|---|---|---|
| Anionic | LAS | 10 |
| | AS | 1 |
| | Soap | 14 |
| Nonionic | AEO | 13 |
| Solvent | 1,2-propane diol | 3 |
| | Ethanol | 5 |
| Buffer | TEA | 6 |
| Builder | Sodium citrate | 1 |
| Neutr, agent NaOH | | 2 |
| Stabilizer etc. SXS | | 1 |
| | $Ca^{2+}$ | 0.0025 |
| | Phosphonate | 0.4 |
| | $Na_2SO_4$ | 0.2 |
| Water | add to 100% | |
| pH | 8 or 10 | |

1000 LU per gram of detergent was added and in some samples 0.025 AU/g (Alcalase®) was added. Samples were stored according to the following scheme (triplicate of each):

| | Storage temperature: | |
|---|---|---|
| | -18° C. | 30° C. |
| | Detergent | |
| pH 8, no protease | 2 & 7 days | 2 & 7 days |
| pH 8, 0.025 AU/g | | 2 days |
| pH 10, no protease | 7 days | 7 days |

Following this incubation the samples were analyzed according to the LU-method (Novo Nordisk AF 95.5).

Assuming that the decay of lipase activity follows a first order kinetic, the rate constant of the decay can be determined:

$$A(t)=A_0*\exp(-k*t)$$

where A(t) is the enzyme activity at time t, $A_0$ the initial activity and k the first order rate constant.

For the detergent containing protease a rate constant for the proteolysis can be calculated from $$A(t)=A_0*\exp(-[k+k_p]*t)$$

where $k_p$ is the rate constant of proteolysis, and k is calculated from the stability data determined in the detergent without protease.

In each experiment the wild-type *H. lanuginosa* lipase was included as a reference, and comparison of the variants with the wild-type is only done within an experiment in order to reduce the uncertainty of variation between experiments.

Below the results are given, and the relative improvement of a variant over the wild-type is given as:

$$IF_x=k_{wt}/k_x$$

where IF means Improvement factor, $k_{wt}$ is the rate constant of decay of the wild-type (at the given conditions) and $k_x$ is the corresponding rate constant of the variant in question in the same experiment.

IF expresses the relative improvement in half-life ($IF_x=2$ indicates that the half-life of variant x is twice as long as that of the wild-type in the same experiment).

Based on an estimation of variations of replicates within an experiment an IF<0.7 or IF>1.3 is considered significant.

The unit of k is (day)$^{-1}$.

| Variant | Experiment no. | | pH 8 no prot. k*) IF*) | pH 8 + Alcalase $k_p$ IF | | pH 10 no prot. k IF | |
|---|---|---|---|---|---|---|---|
| Wildtype | 3 | | 0.02 | 0.48 | | 0.19 | |
| | 5 | | 0.02 | 0.40 | | 0.16 | |
| | 6 | | 0.00 | 0.34 | | 0.09 | |
| | 7 | | 0.01 | 0.52 | | 0.22 | |
| | 8 | a | 0.01 | 0.50 | | 0.09 | |
| | | b | 0.01 | 0.52 | | 0.07 | |
| D96N | 3 | | 0.00 | 0.21 | 2.3 | 0.15 | 1.3 |
| | 5 | | 0.02 | 0.26 | 1.6 | n.d. | |
| D111N | 3 | | 0.00 | 0.50 | 1.0 | 0.16 | 1.2 |
| | 5 | | 0.02 | 0.31 | 1.3 | 0.13 | 1.2 |
| E56Q | 3 | | 0.01 | 0.22 | 2.2 | 0.14 | 1.4 |
| D96L | 6 | | 0.01 | 0.17 | 2.0 | 0.08 | 1.2 |
| | 7 | | 0.00 | 0.23 | 2.3 | 0.09 | 2.6 |
| R209A/E210A/D96L | 7 | | 0.02 | 0.36 | 1.4 | 0.10 | 2.3 |
| E210Q/D242N/D254N | 7 | | 0.02 | 0.49 | 1.0 | n.d. | |
| F211L | 6 | | 0.02 | 0.41 | 0.8 | 0.08 | 1.1 |
| F211T | 8 | | 0.02 | 1.40 | 0.4 | 0.06 | 1.5 |
| F211A | 8 | | 0.01 | 0.58 | 0.9 | 0.02 | 3.1 |
| F211I | 8 | | 0.02 | 1.40 | 0.4 | 0.08 | 1.2 |

*)k in the detergent at pH 8 is in all cases very low, and due to the short storage time (7 days, approx. 90% residual activity) it is not determined very accurately. Hence the IF is not calculated.

In conclusion a number of the tested variants had improved resistance to proteolytic degradation, and they almost all had improved resistance to alkaline conditions.

Example 27

Specific Activity

A higher specific activity (amounts of substrate molecules cleaved pr. unit time pr. unit amount) than the wild-type (wt) was measured for the lipase variants shown below. This means that these lipases have a superior performance of hydrolysing the actual substrate.

The lipases were fermented and purified in the same way. The purified lipases were tested in a standard LU assay (Analytical method, internal NOVO NORDISK number AF 95/6-GB 1991.02.07). The sample was analysed twice, and the mean values are tabulated. The amount of protein was estimated by optical density measurements on a Shimadzu spectrofotometer, using the wave-length 280 nm. The sample was regarded as pure when the proportional value of OD280 divided by OD260 was greater than 1.6, together with a single band SDS-polyacrylamide, gel electrophoresis.

| *Humicola lanuginosa* | Specific activity LU/OD280 |
|---|---|
| D111N | 4290* |
| E56A | 4890* |
| L206V | 4750 |
| F211T | 4550 |
| F211V | 5060 |
| F211I | 6686 |
| R209*/E210* | 6686 |
| R209A/E210A/D96L | 4818 |
| wt | 3790 |

*only tested once

---

We claim:

1. A variant of a lipase having an amino acid sequence of amino acid residues 1–269 of SEQ ID NO:2, comprising one or more deletions or substitutions of an amino acid residue in the lipid contact zone of the lipase.

2. The variant according to claim 1, comprising a deletion of a negatively charged or hydrophilic amino acid residue in the lipid contact zone.

3. The variant according to claim 1, comprising a substitution of a negatively charged amino acid residue in the lipid contact zone with a neutral or positively charged amino acid residue or of a neutral amino acid residue in the lipid contact zone with a positively charged amino acid residue.

4. The variant according to claim 1, wherein the substitution is

E56Q, K, R, A, N, T, S, L, V;
E57A, Q, N, T, S, K, R, L, V;
D62A, Q, N, T, S, K, R, L, V;
E87Q, K, R, A, N, T, S, L, V;
D96N, K, R, A, Q, T, S, L, V;
D111N, K, R, A, Q, T, S, L, V;
E210Q, K, A, A, N, T, S, L, V; or
D254N, K, R, A, Q, T, S, L, V.

5. The variant according to claim 3, wherein the substitution is

S85K, R;
N88K, R;
N92K, R;
I202K, R;
V203K, R;
L206K, R;
I255K, R;
L259K, R; or
T267K, R.

6. The variant according to claim 3, comprising one of the following sets of mutations:

E87Q+D96N+D254N;
E87Q+E210Q+D242N+D254N;
E87Q+E210Q+D254N; or
R209A+E210A.

7. The variant according to claim 1, comprising a substitution of a hydrophilic amino acid residue in the lipid contact zone with a less hydrophilic amino acid residue.

8. The variant according to claim 7, wherein the substitution is

I86V, T, S, A, G;
I90V, T, S, A, G;
L93V, T, S, A, G;
F95L, T, K;
I202V, T, S, A, G;
L206V, T, S, A, G;
F211L, T, K;
I255V, T, S, A, G; or
L259V, T, S, A, G.

9. The variant according to claim 8, wherein the substitution is

I86T;
I90T;
F95K;
L206T;
L206T+I255T+L259T;
I255T; or
L259T.

10. The variant according to claim 1, comprising a substitution of an amino acid residue in the lipid contact zone with a less bulky amino acid residue.

11. The variant according to claim 10, wherein the substitution is

I202V, A, T, S, G;
L206V, A, T, S, G;
F211V, A, T, S, G, I, or
L255V, A, T, S, G.

12. The variant according to claim 1, comprising one of the following sets of mutations:

C22T+L264*+I265*+G266*+T267*+C268*+L269*;
R209*+E210*;
F211*+Y213*;
E239*+I241*+D242*; or
N247*+D254*.

13. The variant according to claim 1, comprising a substitution of a non-aromatic amino acid residue in the lipid contact zone with an aromatic amino acid residue.

14. The variant according to claim 1, wherein the substitution is

E56H, P, M, W, Y, F, I, G, C, V;
D96H, E, P, M, W, Y, F, I, G, C, V;
L206K, R, N, D, C, Q, E, H, I, M, F, P, W, Y; or
L259N, D, C, Q, E, H, I, M, F, P, W, Y.

15. The variant according to claim 1, comprising one of the following sets of mutations:

E56Q+L259I+L206V;
D96L+L206S;
D96L+L206V;
D96L+L206V+L259I;
D96W+D102N;
D96W+E210N; or
D254K+L259I.

16. The variant according to claim 1, comprising a substitution of the amino acid residue at position 58, 83, 94, 98, 129, 205, 252, 256, 263, or 264 with a different amino acid residue.

17. The variant according to claim 1, wherein the substitution is E57G, G61S, S83T, S58F, D62C, I90F, G91A, N92H, N94I, N94K, L97M, K98I, R205K, E210W, N259W, I252L, D254W, P256T, G263A, L264Q or T267W.

18. The variant according to claim 17, wherein the substitution is S83T, N94K, D167G or R205K.

19. The variant according to claim 1, comprising one of the following mutations or sets of mutations:

K46R+E56R+G61S;
E56R+D57G+S58F+D62C+T64R+E87G+G91A+F95L+D96P+K98I+K237M;
E36R+D57L+V60M+D62N+S83T+D96P+D102E;
E56R+I90F+D96L+E99K;
E56T+D57L+I90F+D96L+E99K,
D57G+N94K+D96L+L97M;
N73D+S85T+E87K+G91A+N94K+D96A;
N73D+E87K+G91A+N94I+D96G,
S83T+E87K+W89G+G91A+N94K+D96V;
S83T+E87K+G91A+N92H+N94K+D96M;
S83T+E87K+Q249R;
S83T+N94K+D96N;
E87K+G91A;
E87K+G91A+L93I+N94K+D96A;
E87K+G91A+D96A;
E87K+G91A+D96R+I100V;
E87K+G91A+D96R+I100V+E129K+K237M+I252L+P256T+G263A+L264Q;
E87K+D96V;
G91S+L93V+F95C;
N94K+F95L+D96H;
N94K+D96A;
F95C+D96N;
A121V+R205K+E210Q;
D167G+E210V;
E210V;
E210W; or
N251W+D254W+T267W.

20. The variant according to claim 1, comprising one of the following mutations or sets of mutations:

K46R+E56R+G61S;
E56A;
E56Q;
E56Q+D96L+R209A+E210A;
E56R+D57L+V60M+D62N+S83T+D96P+D102E;
E56R+I90F+D96L+E99K;
D57G+N94K+D96L+L97M;
D57G+N94K+D96L+L97M+E210K;
D57G+N94K+D96L+L97M+Q249R;
N73D+E87K+G91A+N94I+D96G;
S83T+E87K+G91A+N92H+N94K+D96M;
S83T+N94K+D96N;
E87K;
E87K+G91A;
E87K+G91A+L93I+N94K+D96A;
E87K+G91A+D96A;
E87K+G91A+D96R+I100V;
E87K+G91A+D167G+E210V;
E87K+G91A+E210K;
E87K+G91A+Q249R;
E87K+D96V;
E87K+D254K;
E87Q;
N94K+F95L+D96H;
N94K+F95L+D96H+Q249R;
N94K+D96A;
D96F;
D96H;
D96K;
D96L;
D96L+R209A+E210A;
D96N;
D96W;
D96W+D102N;
D102K;
D111N;
D167G;
D167G+E210V;
L206S;
L206T;
L206V;
R209A;
R209A+E210A;
R209*+E210*;
P210K;
E210Q+D242N+D254N;
E210R;
E210W;
F211A;
F211I;
F211L;
P211T;
F211V;
D242N;
N251W+D254W+T267W;
D254K+L259I;
L259I; or
T267R.

21. The variant according to claim 20, wherein the mutation or set of mutations is D57G+N94K+D96L+L97M+E210K.

22. The variant according to claim 20, wherein the mutation or set of mutations is D57G+N94K+D96L+L97M+Q249R.

23. The variant according to claim 20, wherein the mutation or set of mutations is E87K+D254K.

24. The variant according to claim 20, wherein the mutation or set of mutations is D96H.

25. The variant according to claim 20, wherein the mutation or set of mutations is D96K.

26. The variant according to claim 20, wherein the mutation or set of mutations is D96L.

27. The variant according to claim 20, wherein the mutation or set of mutations is R209A.

28. The variant according to claim 20, wherein the mutation or set of mutations is E210K.

29. The variant according to claim 20, wherein the mutation or set of mutations is E210R.

30. A detergent additive comprising a variant according to claim 1 in the form of a non-dusting granulate, stabilized liquid or protected enzyme.

31. A detergent composition comprising a variant according to claim 1 and a surfactant.

32. A dishwashing composition comprising a variant according to claim 1 and a surfactant.

33. A softening composition comprising a variant according to claim 1 and a surfactant.

34. A variant of a Humicola lipase, comprising substitutions of two amino acid residues of the surface loop structure with cysteine which are positioned to form a disulphide bond.

35. The variant according to claim 34, wherein the lipase is a *Humicola lanuginosa* lipase.

36. A variant of lipase having an amino acid sequence of amino acid residues 1–268 of SEQ ID NO:2, comprising substitutions of two amino acid residues of the surface loop structure with cysteine which are positioned to form a disulphide bond.

37. The variant according to claim 36, wherein the substitutions are:
G61C+E87C;
G61C+N88C;
D62C+S85C;
D62C+E87C;
D62C+N88C; or
G91C+S116C.

38. A detergent additive comprising a lipase variant according to claim 34 in the form of a non-dusting granulate, stabilized liquid or protected enzyme.

39. A detergent composition comprising a variant according to claim 34 and a surfactant.

40. A dishwashing composition comprising a variant according to claim 34 and a surfactant.

41. A softening composition comprising a variant according to claim 34 and a surfactant.

42. A variant of a lipase having an amino acid sequence of amino acid residues 1–268 of SEQ ID NO:2, comprising one or more substitutions or deletions at positions: D27, K46, T64, N73, N94, E99, I100, D102, A121, E129, D167, E219, T226, L227, E234, K237, E239 and D242.

43. A variant according to claim 42, comprising a substitution:
D27A, Q, N, T, S, K, R, L, V;
E99A, Q, N, T, S, K, R, L, V;
E219A, Q, N, T, S, K, R, L, V;
T226K, R;
L227K, R;
E234A, Q, N, T, S, K, R, L, V;
5239A, Q, N, T, S, K, R, L, V; or
D242N, K, R, A, Q, T, S, L, V.

44. A variant according to claim 42, comprising one or more of the following substitutions: K46R, T64R, I100V, D102K, A121V, E129K, D167G, or K237M.

45. A variant according to claim 44, comprising one or both of the substitutions D102K and D167G.

46. A detergent additive comprising a lipase variant according to claim 42 in the form of a non-dusting granulate, stabilized liquid or protected enzyme.

47. A detergent composition comprising a variant according to claim 42 and a surfactant.

48. A dishwashing composition comprising a variant according to claim 42 and a surfactant.

49. A softening composition comprising a variant according to claim 42 and a surfactant.

50. A variant of a Humicola lipase, comprising a mutation of an amino acid residue in a lipid contact zone of the lipase, wherein the mutation is selected from the group consisting of:
C22T+L264*+I265*+G266*+T267*C268+L269*;
D27A, Q, N, T, S, K, E, L, V;
K46R+E56R+G61S;
E56Q, K, R, A, N, T, S, L, V, H, P, M, W, Y, F, I, G, C;
E56Q+D96L+R209A+E210A;
E56Q+L259I+L206V;
E56R+D57G+S58F+D62C+T64R+E87G+G91A+F95L+ D96P+K98I+K237M;
E56R+D57L+V60M+D62N+S83T+D96P+D102E;
E56R+I90F+D96L+E99K;
E56T+D57L+I90F+D96L+E99K;
E57A, Q, N, T, S, K, R, L, V;
D57G+N94K+D96L+L97M;
D57G+N94K+D96L+L97M+E210K;
D57G+N94K+D96L+L97M+Q249R;
G61C+E87C;
G61C+N88C;
D62A, Q, N, T, S, K, R, L, V;
D62C+S85C;
D62C+E57C;
D62C+N88C;
N73D+S85T+E87K+G91A+N94K+D96A;
N73D+E87K+G91A+N94I+D96G;
S83T+E87K+W89G+G91A+N94K+D96V;
S83T+E87K+G91A+N92H+N94K+D96M;
S83T+E87K+Q249R;
S83T+N94K+D96N;
S85K, R;
I86V, T, S, A, G;
E87Q, K, R, A, N, T, S, L, V;
E87K+G91A;
E87K+G91A+L93I+N94K+D96A;
E87K+G91A+D96A;
E87K+G91A+D96R+I100V,
E87K+G91A+D96R+I100V+E129K+K237M+I252L+ P256T+G263A+L264Q;
E87K+G91A+D167G+E210V;
E87K+G91A+E210K;
E87K+G91A+Q249R;
E87K+D96V;
E87K+D254K;
E87Q+D96N+D254N;
E87Q+E210Q+D242N+D254N;
E87Q+E210Q+D254N;
N88K, R,
I90V, T, S, A, G;
G91C+S116C;
G91S+L93V+F95C;
N92K, R;
L93V, T, S, A, G;
N94K+F95L+D96H;
N94K+F95L+D96H+Q249R;

N94K+D96A;
F95L, T, K;
F95C+D96N;
D96N, K, R, A, Q, T, S, L, V, H, E, P, M, W, Y, F, I, G, C;
D96L+L206S;
D96L+L206V;
D96L+L206V+L259I;
D96L+R209A+E210A;
D96W+D102N;
D96W+E210N;
E99A, Q, N, T, S, K, R, L, V;
D102K;
D111N, K, R, A, Q, T, S, L, V;
A121V+R205K+E210Q;
D167G;
D167G+E210V;
I202K, R, V, T, S, A, G;
V203K, R;
L206V, T, S, A, G, K, R, N, D, C, Q, E, H, I, M, F, P, W, Y;
L206T+I255T+L259T;
R209A;
R209A+E210A;
R209*+E210*;
E210Q, K, R, A, N, T, S, L, V, W;
E210Q+D242N+D254N;
F211L, T, K, V, A, T, S, G, I;
F211*+Y213*;
E219A, Q, N, T, S, K, R, L, V;
T226K, R;
L227K, R;
E234A, Q, N, T, S, K, R, L, V;
E239A, Q, N, T, S, K, R, L, V;
E239*+I241*+D242*;
D242N, K, R, A, Q, T, S, L, V;
N247*+D254*;
N251W+D254W+T267W;
D254N, K, R, A, Q, T, S, L, V;
D254K+L259I,
I255K, R, V, T, S, A, G,
L259K, R, V, T, S, A, G, N, D, C, Q, E, H, I, M, F, P, W, Y; and
T267K, R;

wherein each position corresponds to a position of the amino acid sequence of SEQ ID NO:2.

51. The variant according to claim 50, wherein the lipase is a *Humicola lanuginosa* lipase.

* * * * *

UNITED STATES PATENT AND TRADEMARK OFFICE
CERTIFICATE OF CORRECTION

PATENT NO. : 5,869,438
APPLICATION NO. : 08/479275
DATED : February 9, 1999
INVENTOR(S) : Svendsen et al.

It is certified that error appears in the above-identified patent and that said Letters Patent is hereby corrected as shown below:

At column 1, line 35, delete "*stearothernophilus*" and insert -- *stearothermophilus* --.

At column 1, line 39, delete "*candidumn*" and insert -- *candidum-* --.

At column 18, line 37, delete "sodium carbonate (as $NaCO_3$)" and insert -- sodium carbonate (as $Na_2Co_3$) --.

At column 19, line 22, delete "$C_{21}\text{-}_{15}$" and insert -- $C_{12-15}$ --.

At column 24, line 33, delete "were foun" and insert -- were found --.

At column 25, line 47, delete "JM102" and insert -- JM101 --.

At column 28, line 30, delete "1 mM DTF" and insert -- 1 mM DTT --.

At column 34, line 20, delete "CGGC3" and insert -- CGGC-3 --.

At column 42, line 66, delete "EZ10W" and insert -- E210K --.

At column 73, line 36, delete "K, A, A," and insert -- K, R, A --.

At column 75, line 16, delete "E36R" and insert -- E56R --.

At column 76, line 34, delete "P210K" and insert -- E210K --.

UNITED STATES PATENT AND TRADEMARK OFFICE
CERTIFICATE OF CORRECTION

PATENT NO. : 5,869,438
APPLICATION NO. : 08/479275
DATED : February 9, 1999
INVENTOR(S) : Svendsen et al.

It is certified that error appears in the above-identified patent and that said Letters Patent is hereby corrected as shown below:

At column 77, line 54, delete "5239A" and insert -- E239A --.

At column 78, line 9, delete "Q, N, T, S, K, E, L, V" and insert
-- Q, N, T, S, K, R, L, V --.

At column 78, line 30, delete "D62C+E57C" and insert -- D62C+E87C --.

Signed and Sealed this

Thirtieth Day of June, 2009

JOHN DOLL
*Acting Director of the United States Patent and Trademark Office*

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 918 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Humicola lanuginosa ( i x ) FEATURE:
        ( A ) NAME/KEY: CDS
        ( B ) LOCATION: 1..873

( i x ) FEATURE:
        ( A ) NAME/KEY: sig_peptide
        ( B ) LOCATION: 1..66

( i x ) FEATURE:
        ( A ) NAME/KEY: mat_peptide
        ( B ) LOCATION: 67..873

( x i ) SEQUENCE DESCRIPTION: SEQ ID NO:1:

```
ATG  AGG  AGC  TCC  CTT  GTG  CTG  TTC  TTT  GTC  TCT  GCG  TGG  ACG  GCC  TTG        4 8
```

```
          Met  Arg  Ser  Ser  Leu  Val  Leu  Phe  Phe  Val  Ser  Ala  Trp  Thr  Ala  Leu
          -22       -20                      -15                           -10

GCC  AGT  CCT  ATT  CGT  CGA  GAG  GTC  TCG  CAG  GAT  CTG  TTT  AAC  CAG  TTC              96
Ala  Ser  Pro  Ile  Arg  Arg  Glu  Val  Ser  Gln  Asp  Leu  Phe  Asn  Gln  Phe
      -5                      1                  5                             10

AAT  CTC  TTT  GCA  CAG  TAT  TCT  GCA  GCC  GCA  TAC  TGC  GGA  AAA  AAC  AAT             144
Asn  Leu  Phe  Ala  Gln  Tyr  Ser  Ala  Ala  Ala  Tyr  Cys  Gly  Lys  Asn  Asn
                    15                      20                      25

GAT  GCC  CCA  GCT  GGT  ACA  AAC  ATT  ACG  TGC  ACG  GGA  AAT  GCC  TGC  CCC             192
Asp  Ala  Pro  Ala  Gly  Thr  Asn  Ile  Thr  Cys  Thr  Gly  Asn  Ala  Cys  Pro
               30                      35                      40

GAG  GTA  GAG  AAG  GCG  GAT  GCA  ACG  TTT  CTC  TAC  TCG  TTT  GAA  GAC  TCT             240
Glu  Val  Glu  Lys  Ala  Asp  Ala  Thr  Phe  Leu  Tyr  Ser  Phe  Glu  Asp  Ser
          45                      50                      55

GGA  GTG  GGC  GAT  GTC  ACC  GGC  TTC  CTT  GCT  CTC  GAC  AAC  ACG  AAC  AAA             288
Gly  Val  Gly  Asp  Val  Thr  Gly  Phe  Leu  Ala  Leu  Asp  Asn  Thr  Asn  Lys
          60                      65                      70

TTG  ATC  GTC  CTC  TCT  TTC  CGT  GGC  TCT  CGT  TCC  ATA  GAG  AAC  TGG  ATC             336
Leu  Ile  Val  Leu  Ser  Phe  Arg  Gly  Ser  Arg  Ser  Ile  Glu  Asn  Trp  Ile
75                       80                      85                           90

GGG  AAT  CTT  AAC  TTC  GAC  TTG  AAA  GAA  ATA  AAT  GAC  ATT  TGC  TCC  GGC             384
Gly  Asn  Leu  Asn  Phe  Asp  Leu  Lys  Glu  Ile  Asn  Asp  Ile  Cys  Ser  Gly
                    95                     100                     105

TGC  AGG  GGA  CAT  GAC  GGC  TTC  ACT  TCG  TCC  TGG  AGG  TCT  GTA  GCC  GAT             432
Cys  Arg  Gly  His  Asp  Gly  Phe  Thr  Ser  Ser  Trp  Arg  Ser  Val  Ala  Asp
               110                     115                     120

ACG  TTA  AGG  CAG  AAG  GTG  GAG  GAT  GCT  GTG  AGG  GAG  CAT  CCC  GAC  TAT             480
Thr  Leu  Arg  Gln  Lys  Val  Glu  Asp  Ala  Val  Arg  Glu  His  Pro  Asp  Tyr
          125                     130                     135

CGC  GTG  GTG  TTT  ACC  GGA  CAT  AGC  TTG  GGT  GGT  GCA  TTG  GCA  ACT  GTT             528
Arg  Val  Val  Phe  Thr  Gly  His  Ser  Leu  Gly  Gly  Ala  Leu  Ala  Thr  Val
     140                     145                     150

GCC  GGA  GCA  GAC  CTG  CGT  GGA  AAT  GGG  TAT  GAT  ATC  GAC  GTG  TTT  TCA             576
Ala  Gly  Ala  Asp  Leu  Arg  Gly  Asn  Gly  Tyr  Asp  Ile  Asp  Val  Phe  Ser
155                      160                     165                          170

TAT  GGC  GCC  CCC  CGA  GTC  GGA  AAC  AGG  GCT  TTT  GCA  GAA  TTC  CTG  ACC             624
Tyr  Gly  Ala  Pro  Arg  Val  Gly  Asn  Arg  Ala  Phe  Ala  Glu  Phe  Leu  Thr
                    175                     180                     185

GTA  CAG  ACC  GGC  GGA  ACA  CTC  TAC  CGC  ATT  ACC  CAC  ACC  AAT  GAT  ATT             672
Val  Gln  Thr  Gly  Gly  Thr  Leu  Tyr  Arg  Ile  Thr  His  Thr  Asn  Asp  Ile
               190                     195                     200

GTC  CCT  AGA  CTC  CCG  CCG  CGC  GAA  TTC  GGT  TAC  AGC  CAT  TCT  AGC  CCA             720
Val  Pro  Arg  Leu  Pro  Pro  Arg  Glu  Phe  Gly  Tyr  Ser  His  Ser  Ser  Pro
          205                     210                     215

GAG  TAC  TGG  ATC  AAA  TCT  GGA  ACC  CTT  GTC  CCC  GTC  ACC  CGA  AAC  GAT             768
Glu  Tyr  Trp  Ile  Lys  Ser  Gly  Thr  Leu  Val  Pro  Val  Thr  Arg  Asn  Asp
     220                     225                     230

ATC  GTG  AAG  ATA  GAA  GGC  ATC  GAT  GCC  ACC  GGC  GGC  AAT  AAC  CAG  CCT             816
Ile  Val  Lys  Ile  Glu  Gly  Ile  Asp  Ala  Thr  Gly  Gly  Asn  Asn  Gln  Pro
235                      240                     245                          250

AAC  ATT  CCG  GAT  ATC  CCT  GCG  CAC  CTA  TGG  TAC  TTC  GGG  TTA  ATT  GGG             864
Asn  Ile  Pro  Asp  Ile  Pro  Ala  His  Leu  Trp  Tyr  Phe  Gly  Leu  Ile  Gly
                    255                     260                     265

ACA  TGT  CTT  TAGTGGCCGG  CGCGGCTGGG  TCCGACTCTA  GCGAGCTCGA  GATCT            918
Thr  Cys  Leu
```

( 2 ) INFORMATION FOR SEQ ID NO:2:

( i ) SEQUENCE CHARACTERISTICS:
        ( A ) LENGTH: 291 amino acids
        ( B ) TYPE: amino acid (D) TOPOLOGY: linear (ii) MOLECULE TYPE: protein (xi) SEQUENCE DESCRIPTION: SEQ ID NO:2:

| Met -22 | Arg | Ser -20 | Ser | Leu | Val | Leu | Phe -15 | Phe | Val | Ser | Ala | Trp -10 | Thr | Ala | Leu |
|---|---|---|---|---|---|---|---|---|---|---|---|---|---|---|---|
| Ala | Ser -5 | Pro | Ile | Arg | Arg | Glu 1 | Val | Ser | Gln | Asp 5 | Leu | Phe | Asn | Gln | Phe 10 |
| Asn | Leu | Phe | Ala | Gln 15 | Tyr | Ser | Ala | Ala | Ala 20 | Tyr | Cys | Gly | Lys | Asn 25 | Asn |
| Asp | Ala | Pro | Ala 30 | Gly | Thr | Asn | Ile | Thr 35 | Cys | Thr | Gly | Asn | Ala 40 | Cys | Pro |
| Glu | Val | Glu 45 | Lys | Ala | Asp | Ala | Thr 50 | Phe | Leu | Tyr | Ser | Phe 55 | Glu | Asp | Ser |
| Gly | Val 60 | Gly | Asp | Val | Thr | Gly 65 | Phe | Leu | Ala | Leu | Asp 70 | Asn | Thr | Asn | Lys |
| Leu 75 | Ile | Val | Leu | Ser | Phe 80 | Arg | Gly | Ser | Arg | Ser 85 | Ile | Glu | Asn | Trp | Ile 90 |
| Gly | Asn | Leu | Asn | Phe 95 | Asp | Leu | Lys | Glu | Ile 100 | Asn | Asp | Ile | Cys | Ser 105 | Gly |
| Cys | Arg | Gly | His 110 | Asp | Gly | Phe | Thr | Ser 115 | Ser | Trp | Arg | Ser | Val 120 | Ala | Asp |
| Thr | Leu | Arg 125 | Gln | Lys | Val | Glu | Asp 130 | Ala | Val | Arg | Glu | His 135 | Pro | Asp | Tyr |
| Arg | Val 140 | Val | Phe | Thr | Gly | His 145 | Ser | Leu | Gly | Gly | Ala 150 | Leu | Ala | Thr | Val |
| Ala 155 | Gly | Ala | Asp | Leu | Arg 160 | Gly | Asn | Gly | Tyr | Asp 165 | Ile | Asp | Val | Phe | Ser 170 |
| Tyr | Gly | Ala | Pro | Arg 175 | Val | Gly | Asn | Arg | Ala 180 | Phe | Ala | Glu | Phe | Leu 185 | Thr |
| Val | Gln | Thr | Gly 190 | Gly | Thr | Leu | Tyr | Arg 195 | Ile | Thr | His | Thr | Asn 200 | Asp | Ile |
| Val | Pro | Arg 205 | Leu | Pro | Pro | Arg | Glu 210 | Phe | Gly | Tyr | Ser | His 215 | Ser | Ser | Pro |
| Glu | Tyr 220 | Trp | Ile | Lys | Ser | Gly 225 | Thr | Leu | Val | Pro | Val 230 | Thr | Arg | Asn | Asp |
| Ile 235 | Val | Lys | Ile | Glu | Gly 240 | Ile | Asp | Ala | Thr | Gly 245 | Gly | Asn | Asn | Gln | Pro 250 |
| Asn | Ile | Pro | Asp | Ile 255 | Pro | Ala | His | Leu | Trp 260 | Tyr | Phe | Gly | Leu | Ile 265 | Gly |
| Thr | Cys | Leu | | | | | | | | | | | | | |

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TTTCTTTCAA CAAGAAGTTA AGA        23

(2) INFORMATION FOR SEQ ID NO:4:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

GTGCGCAGGG ATCTTCGGAA TGTT     24

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GTGCGCAGGG ATTCTCGGAA TGTT     24

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GCCGCCGGTG GCGTTGATGC CTTCTAT     27

( 2 ) INFORMATION FOR SEQ ID NO:7:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GTGCGCAGGG ATGTTCGGAA TGTTAGGCTG GTTATTGCCG CCGGTGGCGT TGATGCCTTC     60

TAT     63

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CCCGATCCAG TTTCTTATCG ATCGAGAGCC GCGG     34

( 2 ) INFORMATION FOR SEQ ID NO:9:

( i ) SEQUENCE CHARACTERISTICS:
        ( A ) LENGTH: 32 base pairs
        ( B ) TYPE: nucleic acid ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CGATCCAGTT CTTTATCGAT CGAGAGCCAC GG 32

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CAGGCGCGCC GGCCACCCGA AGTACCATAG 30

( 2 ) INFORMATION FOR SEQ ID NO:11:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGTCATCCAG TCACTGAGAC CCTCTACCTA TTAAATCGGC 40

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CCATGGCTTT CACGGTGTCT 20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GGTCATCCAG TCACTGAGAC 20

( 2 ) INFORMATION FOR SEQ ID NO:14:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA 5,869,438

-continued ( x i ) SEQUENCE DESCRIPTION: SEQ ID NO:14:

TAGGTGCGCA GGGATCGGAA TGTTAGGCTG GTTGCCGCCG GTGGCATC    48

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

ATTGCCGCCG GTGGCGCCTA TCTTCACGAT ATC    33

( 2 ) INFORMATION FOR SEQ ID NO:16:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..86

( x i ) SEQUENCE DESCRIPTION: SEQ ID NO:16:

```
CT AGG GTT CCG CCG CGC GAA TTC GGT TAC AGC CAT TCT AGC CCA GAA    47
   Arg Val Pro Pro Arg Glu Phe Gly Tyr Ser His Ser Ser Pro Glu
   1               5                   10                  15

TAC TGG ATC AAA TCT GGA ACC CTT GTC CCC GTC ACG CGC                86
Tyr Trp Ile Lys Ser Gly Thr Leu Val Pro Val Thr Arg
            20                  25
```

( 2 ) INFORMATION FOR SEQ ID NO:17:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Arg Val Pro Pro Arg Glu Phe Gly Tyr Ser His Ser Ser Pro Glu Tyr
1               5                   10                  15

Trp Ile Lys Ser Gly Thr Leu Val Pro Val Thr Arg
            20                  25
```

( 2 ) INFORMATION FOR SEQ ID NO:18:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

ATTCCCGATC CAGTTACATA TGGAACGAGA GCCACGGAAG CTTAGGACGA TCAATTTGTT    60

CGTGTTGTCG AGAGCAAGGA AGCCGGTGAC ACAGCCCACT CCAGAGTC    108

( 2 ) INFORMATION FOR SEQ ID NO:19:

( i ) SEQUENCE CHARACTERISTICS:
　　　　( A ) LENGTH: 40 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:19:

GGTCATCCAG TCACTGAGAC CCTCTACCTA TTAAATCGGC　　　　　　　　　　　　40

( 2 ) INFORMATION FOR SEQ ID NO:20:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:20:

CCATGGCTTT CACGGTGTCT　　　　　　　　　　　　20

( 2 ) INFORMATION FOR SEQ ID NO:21:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:21:

GGTCATCCAG TCACTGAGAC　　　　　　　　　　　　20

( 2 ) INFORMATION FOR SEQ ID NO:22:

( i ) SEQUENCE CHARACTERISTICS:
　　　　( A ) LENGTH: 114 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:22:

AAGATTCCCG ATCCAACACT CTATGGAACG AGAGCCACGG AAGCTTAGGA CGATCAATTT　　　60

GTTCGTGTTG TCGAGAGCAA GGAAGCCGGT GACATCACAC ACTCCAGAGT CTTC　　　114

( 2 ) INFORMATION FOR SEQ ID NO:23:

( i ) SEQUENCE CHARACTERISTICS:
　　　　( A ) LENGTH: 44 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:23:

TAACCCGAAG TACCAAGTGT GCGCAGGAGT ATCCGGAATG TTAG　　　　　　　　　　　　44

( 2 ) INFORMATION FOR SEQ ID NO:24:

( i ) SEQUENCE CHARACTERISTICS:

(A) LENGTH: 86 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 3..86

(xi) SEQUENCE DESCRIPTION: SEQ ID NO:24:

```
CT AGG GTT CCG CCG CGC GAA TTC GGT TAC AGC CAT TCT AGC CCA GAA        47
   Arg Val Pro Pro Arg Glu Phe Gly Tyr Ser His Ser Ser Pro Glu
   1               5                   10                  15

TAC TGG ATC AAA TCT GGA ACC CTT GTC CCC GTC ACG CGC                   86
Tyr Trp Ile Lys Ser Gly Thr Leu Val Pro Val Thr Arg
                20                  25
```

(2) INFORMATION FOR SEQ ID NO:25:

(i) SEQUENCE CHARACTERISTICS:
            (A) LENGTH: 28 amino acids
            (B) TYPE: amino acid
            (D) TOPOLOGY: linear (ii) MOLECULE TYPE: protein (xi) SEQUENCE DESCRIPTION: SEQ ID NO:25:

```
Arg Val Pro Pro Arg Glu Phe Gly Tyr Ser His Ser Ser Pro Glu Tyr
1               5                   10                  15

Trp Ile Lys Ser Gly Thr Leu Val Pro Val Thr Arg
            20                  25
```

(2) INFORMATION FOR SEQ ID NO:26:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:26:

```
TCTTTCAAGT TGAAGTTAAG A                                               21
```

(2) INFORMATION FOR SEQ ID NO:27:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:27:

```
GTGAAGCCGT TATGTCCCCT G                                               21
```

(2) INFORMATION FOR SEQ ID NO:28:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA ( x i ) SEQUENCE DESCRIPTION: SEQ ID NO:28:

CGATCCAGTT TTGTATGGAA CGA 23

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

GCTGTAACCG AAAGCAGCCG GCGGGAGTCT 30

( 2 ) INFORMATION FOR SEQ ID NO:30:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

CGATCCAGTT AGCTATGGAA CG 22

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

CTCCAGAGTC AGCAAACGAG TA 22

( 2 ) INFORMATION FOR SEQ ID NO:32:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

CCAGAGTCTT GAAACGAGTA G 21

( 2 ) INFORMATION FOR SEQ ID NO:33:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

AAGTGAAGCC CAAATGTCCC CTG 23

( 2 ) INFORMATION FOR SEQ ID NO:34:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

TGTAACCGAA AGCGCGCGGC GG      22

( 2 ) INFORMATION FOR SEQ ID NO:35:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

TAACCGAATT GGCGCGGCGG G      21

( 2 ) INFORMATION FOR SEQ ID NO:36:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

AACCGAATTC AGCCGGCGGG AGT      23

( 2 ) INFORMATION FOR SEQ ID NO:37:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

GTGCGCAGGG ATGTTCGGAA TGTTAGG      27

( 2 ) INFORMATION FOR SEQ ID NO:38:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

ATTTATTTCT TTCAACCAGA AGTTAAGATT CCC      33

( 2 ) INFORMATION FOR SEQ ID NO:39:

( i ) SEQUENCE CHARACTERISTICS:
        ( A ) LENGTH: 33 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:39:

ATTTATTTCT TTCAAGAAGA AGTTAAGATT CCC    33

( 2 ) INFORMATION FOR SEQ ID NO:40:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:40:

ATTTATTTCT TTCAAAACGA AGTTAAGATT CCC    33

( 2 ) INFORMATION FOR SEQ ID NO:41:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:41:

CCGAAGTACC AAATGTGAGC AGGGATATCC    30

( 2 ) INFORMATION FOR SEQ ID NO:42:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:42:

CCGAAGTACC AAATGTGAGC AGGGATCTTC GGAATGTTAG G    41

( 2 ) INFORMATION FOR SEQ ID NO:43:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:43:

TATTTCTTTC AAAGCGAACT TAAGATTCCC GAT    33

( 2 ) INFORMATION FOR SEQ ID NO:44:

( i ) SEQUENCE CHARACTERISTICS:
( A ) LENGTH: 65 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:44:

ATTTCTTTCA AAGCGAACTT AAGATTCCCG ATCCAGTTCT CTATGGAACG AGTGCCACGG    60

AAAGA    65

( 2 ) INFORMATION FOR SEQ ID NO:45:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

TATTTCTTTC AAAACGAAGT TAAGATTCCC GATCCAGTTC TTTATGGAAC GAGA    54

( 2 ) INFORMATION FOR SEQ ID NO:46:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

TATTTCTTTC AAAGCGAAGT TAAGATTAGC GATCCAGTTC TTTATGGAAC GAGA    54

( 2 ) INFORMATION FOR SEQ ID NO:47:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

TATTTCTTTC AAGTGCAACT TAAGATTCCC GAT    33

( 2 ) INFORMATION FOR SEQ ID NO:48:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

TATTTCTTTC AAGTTACAGT TAAGATTCCC    30

( 2 ) INFORMATION FOR SEQ ID NO:49:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

TATTTCTTTC AAGTCACAGT TAACATTAGA GATCCAGTTC TC    42

( 2 ) INFORMATION FOR SEQ ID NO:50:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

TATTTCTTTC AAAGCGAACT TAATATTAGC GATCCAGTTC TTTATGGAAC GAGA     54

( 2 ) INFORMATION FOR SEQ ID NO:51:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

ATATGAAAAC ACACCGATAT CATACCC     27

( 2 ) INFORMATION FOR SEQ ID NO:52:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

CCTTAACGTA TCAACTACAG ACCTCCA     27

( 2 ) INFORMATION FOR SEQ ID NO:53:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

GCTGTAACCG AATTGGCGCG GCGGGAGCTT AGGGACAATA TC     42

( 2 ) INFORMATION FOR SEQ ID NO:54:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

TATTTCTTTC AAAGCGAACT TAAGATTAGC GATCCAGTTC TTTATAGTAC GAGAGCCACG     60

GAAAGAGAGG ACGATCAATT TGTCCGTGTT GTCGAG     96

( 2 ) INFORMATION FOR SEQ ID NO:55:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:55:

TATTTCTTTC AAAACGAACT TAAGATTAGC GATACCGTTC TTTATGGAAC GAGTGCCACG 60

GAAAGA 66

( 2 ) INFORMATION FOR SEQ ID NO:56:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:56:

GCAAATGTCA TTAACTTCTT TCAATCTGAA GTTAAGATTA GCGATCCAGT TCTTTATGGA 60

ACGAGA 66

( 2 ) INFORMATION FOR SEQ ID NO:57:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:57:

CCCGATCCAG TTCTTTATGG AACGAGTGCC ACGGAAAGA 39

( 2 ) INFORMATION FOR SEQ ID NO:58:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:58:

GAAGTTAAGA TTAGCGATCC AGTTCTTTAT GGAACGAGA 39

( 2 ) INFORMATION FOR SEQ ID NO:59:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:59:

CCCGATCCAG TTCTTTATGG AACGAGTGCC ACGGAAAGA 39

( 2 ) INFORMATION FOR SEQ ID NO:60:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:60:

CGGAATGTTA GGTCTGTTAT TGCCGCC        27